US009000134B2

(12) United States Patent
Haigh et al.

(10) Patent No.: US 9,000,134 B2
(45) Date of Patent: Apr. 7, 2015

(54) REAGENT AND KIT FOR EARLY DIAGNOSIS OF KIDNEY DISEASE

(76) Inventors: Wallace B. Haigh, Madison, CT (US); Donald L. Very, Jr., Little Silver, NJ (US)

( * ) Notice: Subject to any disclaimer, the term of this patent is extended or adjusted under 35 U.S.C. 154(b) by 1284 days.

(21) Appl. No.: 12/119,238

(22) Filed: May 12, 2008

(65) Prior Publication Data

US 2009/0023165 A1    Jan. 22, 2009

Related U.S. Application Data

(60) Provisional application No. 60/917,634, filed on May 11, 2007.

(51) Int. Cl.
| | | |
|---|---|---|
| G01N 33/535 | (2006.01) | |
| C07K 16/18 | (2006.01) | |
| C07K 16/28 | (2006.01) | |
| C07K 16/36 | (2006.01) | |
| C07K 16/38 | (2006.01) | |
| C07K 16/40 | (2006.01) | |
| C07K 16/42 | (2006.01) | |
| G01N 33/68 | (2006.01) | |
| G01N 33/58 | (2006.01) | |
| G01N 33/573 | (2006.01) | |

(52) U.S. Cl.
CPC .......... *G01N 33/6893* (2013.01); *G01N 33/535* (2013.01); *G01N 33/581* (2013.01); *C07K 16/36* (2013.01); *C07K 16/38* (2013.01); *C07K 16/18* (2013.01); *C07K 16/2896* (2013.01); *C07K 16/40* (2013.01); *C07K 16/42* (2013.01); *G01N 33/6854* (2013.01); *G01N 2570/00* (2013.01); *G01N 33/6827* (2013.01); *G01N 33/573* (2013.01); *G01N 2800/042* (2013.01); *G01N 2800/347* (2013.01); *Y10S 435/975* (2013.01); *Y10S 530/834* (2013.01)

(58) Field of Classification Search
CPC .... A61K 39/0005; C07K 16/18; C07K 16/36; C07K 16/38; C07K 16/40; C07K 16/42; C07K 17/02; C07K 2316/50; C07K 2317/10; C07K 2317/515; C07K 16/2896; G01N 33/535; G01N 33/537; G01N 33/54306; G01N 33/54386; G01N 33/545; G01N 33/573; G01N 33/581; G01N 33/6827; G01N 33/6857; G01N 2030/143; G01N 2333/435; G01N 2333/46; G01N 2333/4728; G01N 2333/70596; G01N 2333/765; G01N 2333/96425; G01N 2333/96477; G01N 2333/974; G01N 2570/00; G01N 2800/042; G01N 2800/347; G01N 2800/50; G01N 33/6854; G01N 33/6893
USPC ............ 435/7.1, 7.92, 7.93, 7.95, 70.21, 336, 435/337, 338, 975; 436/518, 523, 528, 531, 436/547, 548, 164, 811; 530/350, 388.24, 530/388.25, 388.26, 389.2, 389.3, 391.1, 530/395, 806, 834
See application file for complete search history.

(56) References Cited

U.S. PATENT DOCUMENTS

| | | | |
|---|---|---|---|
| 5,879,897 A | 3/1999 | Koufman | |
| 6,087,182 A | 7/2000 | Jeng et al. | |
| 6,589,748 B2 * | 7/2003 | Comper | ........................ 435/7.1 |
| 6,773,922 B2 | 8/2004 | Jeng et al. | |
| 6,835,545 B2 | 12/2004 | Halperin | |
| 6,969,591 B2 * | 11/2005 | Hara | .............................. 435/7.1 |
| 7,049,082 B2 | 5/2006 | Halperin | |
| 7,109,044 B1 | 9/2006 | Oda et al. | |
| 7,172,873 B2 | 2/2007 | McDonald et al. | |
| 7,258,775 B2 | 8/2007 | Mischak et al. | |
| 7,303,922 B2 | 12/2007 | Jeng et al. | |
| 7,456,027 B2 | 11/2008 | Wang et al. | |
| 7,662,578 B2 * | 2/2010 | Devarajan | .................... 435/7.21 |
| 7,713,705 B2 | 5/2010 | Buechler et al. | |
| 2003/0003588 A1 | 1/2003 | Comper | |
| 2003/0027216 A1 | 2/2003 | Kiernan et al. | |
| 2003/0032017 A1 | 2/2003 | Anderson et al. | |
| 2005/0026225 A1 | 2/2005 | Comper | |
| 2005/0191664 A1 * | 9/2005 | Comper | ........................... 435/6 |
| 2006/0127948 A1 | 6/2006 | Kiernan et al. | |
| 2006/0166293 A1 | 7/2006 | Hale et al. | |
| 2006/0286602 A1 | 12/2006 | Mischak et al. | |
| 2007/0087387 A1 | 4/2007 | Devarajan | |
| 2007/0105149 A1 * | 5/2007 | Walsh et al. | ................... 435/7.1 |
| 2008/0153092 A1 | 6/2008 | Kienle et al. | |
| 2008/0206794 A1 | 8/2008 | Hu et al. | |
| 2008/0227117 A1 | 9/2008 | Fehniger et al. | |
| 2009/0004687 A1 | 1/2009 | Mansfield et al. | |
| 2009/0081713 A1 | 3/2009 | Klein et al. | |
| 2009/0098583 A1 | 4/2009 | McDonald et al. | |

(Continued)

FOREIGN PATENT DOCUMENTS

| | | |
|---|---|---|
| WO | WO 98/12349 | 3/1998 |
| WO | WO 03/002757 | 1/2003 |

(Continued)

OTHER PUBLICATIONS

Jain et al., 2005. Proteomic analysis of urinary protein markers for accurate prediction of diabetic kidney disorder. J. Assoc. Phys. India 53: 513-520.*

Nakamura et al., 2000. Urinary excretion of podocytes in patients with diabetic nephropathy. Nephrol. Dial. Transplant. 15: 1379-1383.*

Grant, 1959. The proteins of normal urine. II. From the urinary tract. J. Clin. Pathol. 12: 510-517.*

Bakker et al. (2005), "Altered activity of plasma hemopexin in patients with minimal change disease in relapse." Pediatr Nephrol. 20(10):1410-5.

(Continued)

*Primary Examiner* — Gail R Gabel
*Assistant Examiner* — James L Grun
(74) *Attorney, Agent, or Firm* — McDonnell Boehnen Hulbert & Berghoff LLP

(57) ABSTRACT

The invention provides reagents and methods for diagnosing kidney disease in a human or animal.

23 Claims, 18 Drawing Sheets

(56) References Cited

U.S. PATENT DOCUMENTS

| | | |
|---|---|---|
| 2009/0191574 A1 | 7/2009 | Halperin |
| 2009/0238812 A1 | 9/2009 | Kilty et al. |
| 2009/0239242 A1 | 9/2009 | Kilty et al. |
| 2009/0258830 A1 | 10/2009 | Thadhani et al. |
| 2009/0298073 A1 | 12/2009 | Gerhold et al. |
| 2010/0008899 A1 | 1/2010 | Williams |
| 2010/0120056 A1 | 5/2010 | Bar-Or et al. |

FOREIGN PATENT DOCUMENTS

| | | |
|---|---|---|
| WO | WO 03/014737 | 2/2003 |
| WO | WO 2005/113798 | 12/2005 |
| WO | WO 2006/009533 | 1/2006 |
| WO | WO 2006/118522 | 11/2006 |
| WO | WO 2007/024825 | 3/2007 |
| WO | WO 2007/124419 | 11/2007 |
| WO | WO 2007/148720 | 12/2007 |
| WO | WO 2008/011713 | 1/2008 |
| WO | WO 2008/047086 | 4/2008 |
| WO | WO 2008/092094 | 7/2008 |
| WO | WO 2008/092214 | 8/2008 |
| WO | WO 2008/099279 | 8/2008 |
| WO | WO 2008/134526 | 11/2008 |
| WO | WO 2009/006439 | 1/2009 |
| WO | WO 2009/024070 | 2/2009 |
| WO | WO 2009/059259 | 5/2009 |
| WO | WO 2009/094194 | 7/2009 |
| WO | WO 2010/005387 | 1/2010 |

OTHER PUBLICATIONS

Bergsland et al. (2006), "Urine protein markers distinguish stone-forming from non-stone-forming relatives of calcium stone formers." Am J Physiol Renal Physiol. 291(3):F530-6.

Bernard et al. (1989), "Urine protein 1: a sex-dependent marker of tubular or glomerular dysfunction." Clin Chem. 35 (10):2141-2.

Bernard et al. (1994), "Urinary protein 1 or Clara cell protein: a new sensitive marker of proximal tubular dysfunction." Kidney Int Suppl. 47:S34-7.

Bürgi et al. (1989), "Unusually high concentrations of Zn alpha 2-glycoprotein and the lack of alpha 2HS-glycoprotein in human ejaculates." Clin. Chem. 35(8): 1649-50.

Flynn et al. (1992), "Urinary excretion of beta 2-glycoprotein-1 (apolipoprotein H) and other markers of tubular malfunction in "non-tubular" renal disease." J Clin Pathol. 45(7):561-7.

Hale et al. (2001), "Zinc alpha-2-glycoprotein is expressed by malignant prostatic epithelium and may serve as a potential serum marker for prostate cancer." Clin. Cancer. Res. 7(4): 846-53.

Hoffmann et al. (1997), "Molecular characterization of beta-trace protein in human serum and urine: a potential diagnostic marker for renal diseases." Glycobiology. 7(4):499-506.

Igarashi et al. (1993), "An enzyme-linked immunosorbent assay for urinary albumin in patients with insulin-dependent diabetes mellitus." J. Ped. Endocrinol. 6(2): 159-64.

International Search Report from International Application No. PCT/US2008/063429, International Publication No. WO/2008/141285, mailed Jan. 27, 2009.

Joh et al. (1990), "Microlamellar structures in lobular glomerulonephritis associated with monoclonal IgG lambda paraproteinemia. A case report and review of the literature." Acta Pathol Jpn. 40(12):913-21.

Kebler et al. (1985), "Rapidly progressive glomerulonephritis and monoclonal gammopathy." Am J Med. 78(1):133-8.

Kitamoto et al. (2004), "Assessment of thrombin in the urine of glomerulonephritic patients by enzyme-linked immunosorbent assay." Ann Clin Biochem. 41(Pt 2):133-7.

Lehto et al. (1995), "Urinary excretion of protectin (CD59), complement SC5b-9 and cytokines in membranous glomerulonephritis." Kidney Int. 47(5):1403-11.

Nakatsuka et al. (2005), "A case of monoclonal immunoglobulin light- and heavy-chain deposition disease exhibiting atypical deposition with fibrillary structures, successfully treated with chemotherapy." Clin Nephrol. 64(3):221-7.

Nakayashiki (1990), "Sweat protein components tested by SDS-polyacrylamide gel electrophoresis followed by immunoblotting." Tohoku Journal of Experimental Medicine 161(1): 25-31.

Qi and Chen (1985), "[Analysis of measured results of urinary pepsin and 17-OHCS in chronic gastritis with splenic and renal insufficiency based on Chinese traditional medicine]" [in Chinese]. Zhong Xi Yi Jie He Za Zhi. 5(1):27-9, 3. [English abstract.].

Rakov and Betekhitina (2000), "[Protein markers in evaluation of nephroprotective effects of antihypertensive drugs in patients with arterial hypertension]" [Article in Russian with English abstract]. Klin Lab Diagn. (7):3-7.

Rampino et al. (2007), "Neutralization of macrophage-stimulating protein ameliorates renal injury in anti-thy 1 glomerulonephritis." J Am Soc Nephrol. 18(5):1486-96.

Rao et al. (2007), "Proteomic Identification of Urinary Biomarkers of Diabetic Nephropathy." Diabetes Care 30:629-37.

Simoni et al. (2006), "Role of free hemoglobin in 8-iso prostaglandin F2-alpha synthesis in chronic renal failure and its impact on CD163-Hb scavenger receptor and on coronary artery endothelium." ASAIO J. 52(6):652-61.

Sobajima et al. (1998), "Urinary excretion of pancreatic stone protein in diabetic nephropathy." Intern Med. 37 (6):500-3.

Tashiro et al. (2002), "Urinary levels of monocyte chemoattractant protein-1 (MCP-1) and interleukin-8 (IL-8), and renal injuries in patients with type 2 diabetic nephropathy." J. Clin. Lab. Analysis 16(1): 1-4.

Tomlinson et al. (1997), "Low molecular weight protein excretion in glomerular disease: a comparative analysis." Pediatr Nephrol. 11(3):285-90.

Valleix et al. (2002), "Hereditary renal amyloidosis caused by a new variant lysozyme W64R in a French family." Kidney Int. 61(3):907-12.

Varghese et al. (2007), "Urine biomarkers predict the cause of glomerular disease." J Am Soc Nephrol. 18 (3):913-22.

Weinberg et al. (1985), "The role of urinary kininogen in the regulation of kinin generation." Kidney Int. 28(6):975-81.

Weinberg et al. (1986), "Urinary kininogen: a possible regulator of kinin formation in normal individuals and subjects with essential hypertension, end-stage renal and liver disease." Adv Exp Med Biol. 198 Pt A:119-25.

Written Opinion of the International Searching Authority from International Application No. PCT/US2008/063429, International Publication No. WO/2008/141285, dated Dec. 21, 2008.

* cited by examiner

IBA-GA Lot 022 LC-MS/MS Results

Solution Tryptic Digest of Lot 2 GA without Trf and IgG

| Yale | | | Protana | | |
|---|---|---|---|---|---|
| Protein ID | # of Peptides | Score | Protein ID | # of Peptides | Score |
| zinc Alpha-2-glycoprotein | 14 | 843 | zinc Alpha-2-glycoprotein | 11 | 187 |
| AMBP (alpha-1 microglobulin) | 13 | 879 | AMBP (alpha-1 microglobulin) | 9 | 177 |
| Alpha-1-acid glycoprotein 1 | 7 | 432 | IgG Kappa chain (IGKV 1-5) | 5 | 100 |
| Alpha-1-acid glycoprotein 2 | 6 | 311 | Alpha-1-acid glycoprotein 1 | 4 | 68 |
| IgG Kappa chain (IGKV 1-5) | 6 | 600 | Kininogen | 4 | 68 |
| IgG Lambda chain | 6 | 319 | Haptoglobin | 4 | 52 |
| Prostaglandin-H2 D-isomerase precursor | 4 | 336 | Prostaglandin-H2 D-isomerase precursor | 3 | 52 |
| HGFL protein | 4 | 236 | Tamm-HorsFall glycoprotein | 3 | 55 |
| Urine protein1 | 3 | 222 | Saposin precursor | 3 | 54 |
| Complement reg. protein CD59 | 3 | 210 | gelsolin | 3 | 49 |
| Thrombin | 3 | 183 | Hemopexin | 3 | 46 |
| Hemopexin | 3 | 150 | Pancreatic stone protein | 3 | 43 |
| Alpha-2-HS-glycoprotein precursor | 3 | 224 | WAP-Whey acid protein | 3 | 42 |
| G(M2) activator protein | 2 | 109 | G(M2) activator protein | 3 | 55 |
| Pancreatic stone protein | 2 | 104 | Alpha-1-acid glycoprotein 2 | 2 | 27 |
| Saposin precursor | 2 | 102 | Pepsin | 2 | 27 |
| Pepsin | 2 | 81 | HGFL protein | 2 | 34 |
| Kininogen | 2 | 65 | IgG Lambda chain | 2 | 31 |
| Alpha-1B-glycoprotein | 2 | 102 | | | 30 |
| 90 kD protein | 1 | 90 | | | |
| Beta-trace 23kD glycoprotein | | 74 | | | |
| Haptoglobin | not found by Yale | | Urine protein1 | not found by Protana | |
| Tamm-HorsFall glycoprotein | not found by Yale | | Thrombin | not found by Protana | |
| gelsolin | not found by Yale | | Alpha-2-HS-glycoprotein precursor | not found by Protana | |
| WAP-Whey acid protein | not found by Yale | | Alpha-1B-glycoprotein | not found by Protana | |
| | | | 90 kD protein | not found by Protana | |
| | | | Beta-trace 23kD glycoprotein | not found by Protana | |

FIGURE 5

Relative Abundance as Estimated by # of Peptides
Summary and Comparison of 2 LC-MS/MS Gel Experiments

| All Gel1 LOT2GA Protein Ids – Ranked by Score | | | All Gel2 LOT2GA Protein Ids – Ranked by Score | | |
|---|---|---|---|---|---|
| Protein ID | Score | # of Peptides | Protein ID | Score | # of Peptides |
| Serotransferrin precursor | 1470 | 89 | Serotransferrin precursor | 1830 | 59 |
| AMBP (alpha-1 microglobulin) | 935 | 40 | zinc Alpha-2-glycoprotein | 756 | 29 |
| IgG Kappa chain (IGKV1-5) | 441 | 15 | AMBP (alpha-1 microglobulin) | 479 | 19 |
| Zinc Alpha-2-glycoprotein | 324 | 32 | IgG Heavy Chain | 358 | 13 |
| Alpha-1-acid glycoprotein 1 | 297 | 23 | IgG Gamma-1 Chain | 345 | 12 |
| IgG Lambda Chain | 269 | 14 | Alpha-1-acid glycoprotein 1 | 293 | 12 |
| Alpha-1-acid glycoprotein 2 | 260 | 19 | IgG Gamma-4 Chain | 284 | 12 |
| IgG Alpha-1 Chain | 180 | 12 | IgG Alpha-1 Chain | 269 | 8 |
| IgG Gamma-4 Chain | 174 | 15 | Alpha-1-acid glycoprotein 2 | 228 | 12 |
| Alpha-1-antitrypsin precursor | 163 | 11 | IgG Kappa chain (IGKV 1-5) | 220 | 5 |
| Prostaglandin-H2 D-isomerase | 147 | 6 | Complement reg. protein CD59 | 146 | 5 |
| Agrin precursor | 137 | 2 | Prostaglandin-H2 D-isomerase | 134 | 2 |
| Splice isoform 2 of EGF | 135 | 4 | G(M2) activator protein | 129 | 4 |
| Kininogen precursor | 115 | 6 | Saposin | 126 | 3 |
| Beta-2-glycoprotein 1 | 97 | 6 | IgG Lambda Chain | 121 | 5 |
| Lithostathine-1-alpha precursor | 95 | 6 | HGFL | 102 | 3 |
| Alpha-2-HS-glycoprotein precursor | 85 | 8 | Vascular cell adhesion protein 1 | 99 | 3 |
| Apolipoprotein D precursor | 82 | 2 | Urine protein 1 | 92 | 4 |
| CD44 | 82 | 2 | Haptoglobin precursor | 80 | 2 |
| Major prion protein precursor | 79 | 2 | Gelsolin | 77 | 2 |
| Haptoglobin precursor | 70 | 4 | Alpha-1-antitrypsin precursor | 70 | 3 |

FIGURE 7

| Protein ID | Score | # of Peptide |
|---|---|---|
| Calgranulin B | 66 | 2 |
| Calgranulin A | 57 | 1 |
| Vascular cell adhesion protein 1 | 55 | 4 |
| IgG Heavy Chain | not found in gel1 | |
| IgG Gamma-1 Chain | not found in gel1 | |
| Complement reg. protein CD59 | not found in gel1 | |
| G(M2) activator protein | not found in gel1 | |
| Saposin | not found in gel1 | |
| HGFL | not found in gel1 | |
| Urine protein 1 | not found in gel1 | |
| Gelsolin | not found in gel1 | |
| Beta-trace 23kD glycoprotein | not found in gel1 | |
| Thrombin | not found in gel1 | |
| Prostasin | not found in gel1 | |
| Saposin | not found in gel1 | |
| Serum albumin precursor | not found in gel1 | |

| Protein ID | Score | # of Peptide |
|---|---|---|
| Beta-trace 23kD glycoprotein | 69 | 1 |
| Apolipoprotein D precursor | 66 | 1 |
| Thrombin | 57 | 1 |
| Prostasin | 56 | 1 |
| Saposin | 52 | 2 |
| Serum albumin precursor | 50 | 1 |
| Alpha-2-HS-glycoprotein precursor | 45 | |
| Kininogen precursor | not found in gel2 | |
| Lithostathine 1 alpha precursor | not found in gel2 | |
| Calgranulin A | not found in gel2 | |
| Calgranulin B | not found in gel2 | |
| Splice isoform 2 of EGF | not found in gel2 | |
| Beta-2-glycoprotein 1 | not found in gel2 | |
| Hypothetical protein DKFZp686C152 | not found in gel2 | |
| CD44 | not found in gel2 | |
| Agrin precursor | not found in gel2 | |
| Major prion protein precursor | not found in gel2 | |

* keratin excluded

FIGURE 7 (cont'd)

Comparison of Starting Material (SM) before anti-HSA column and of GA001 and GA002.

HSA and Urinary Protein ELISA Standard Curves
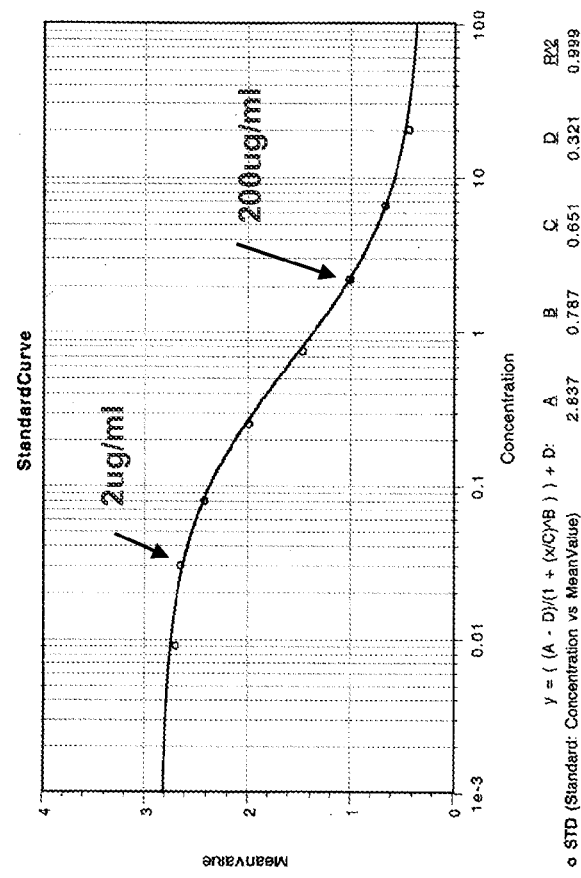
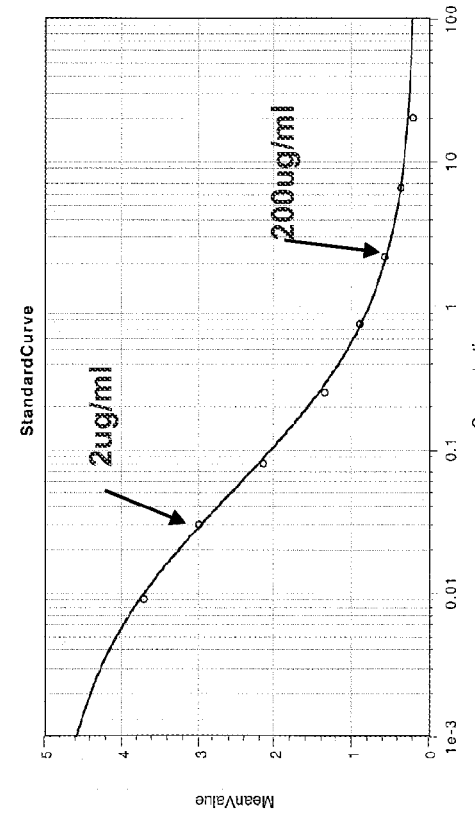
FIGURE 13

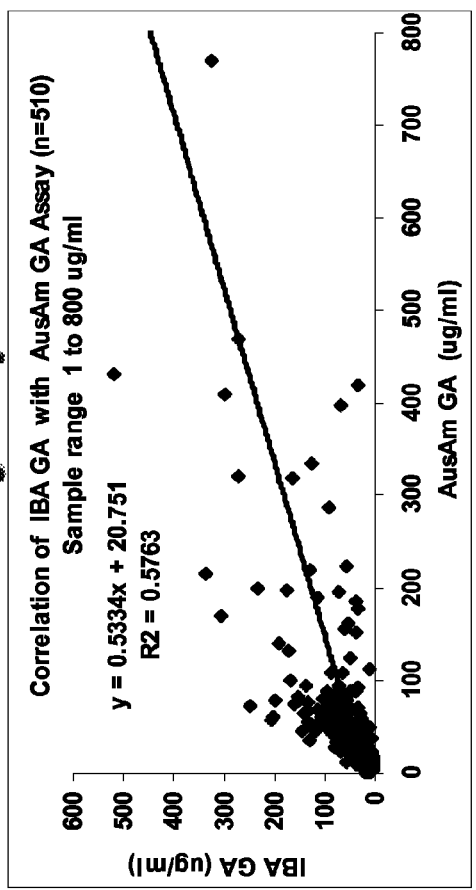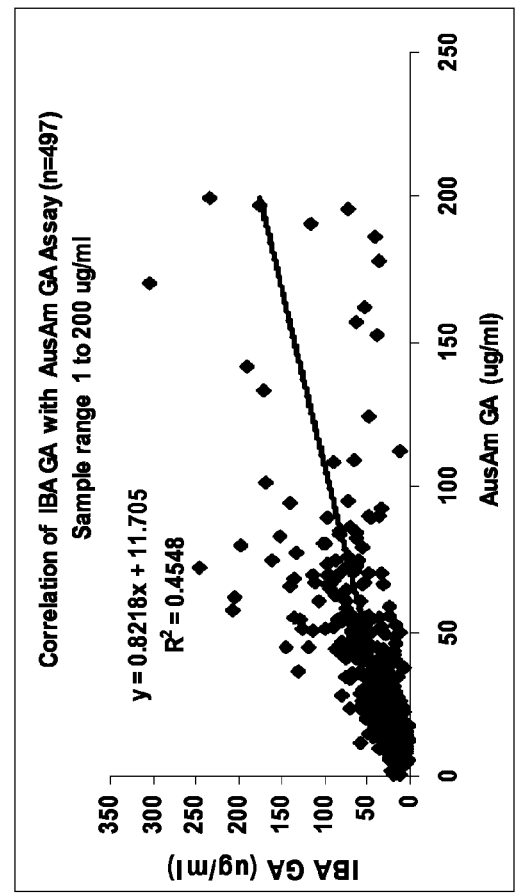
Figure 16

REAGENT AND KIT FOR EARLY DIAGNOSIS OF KIDNEY DISEASE

BACKGROUND OF THE INVENTION

1. Field of the Invention

The invention provides reagents and methods for diagnosing kidney disease in a human or animal. In particular, the reagents of the invention comprise immunological reagents, including polyclonal antisera or one or a plurality of monoclonal antibodies, immunologically-specific for proteins and/or peptides in urine, preferably humans with diabetes. The invention provides methods for using these reagents for performing diagnostic and prognostic assays for identifying individuals, particularly humans with diabetes with kidney disease or at risk for kidney disease. The invention also provides kits comprising the diagnostic reagents of the invention for performing the diagnostic methods of the invention.

2. Background of the Related Art

Kidney disease is a significant source of morbidity and mortality in the United States, with more than 100,000 people diagnosed with kidney failure each year. Kidney failure is the final stage of kidney disease, also known as nephropathy. The economic cost of kidney disease is high, costing more than $27 million annually.

The most common cause of kidney failure is diabetes, which affects about 18 million people in the U.S. Diabetes accounts for nearly 45 percent of new cases of kidney failure, and about 30 percent of patients with Type I (juvenile onset) diabetes and 10 to 40 percent of those with Type 2 (adult onset) diabetes will eventually have kidney failure. On average it takes a person with diabetes over 20 years to progress to the end stage.

Kidney failure and nephropathy can occur even when diabetes is controlled. Fortunately, most people with diabetes do not develop nephropathy that is severe enough to cause kidney failure. Unfortunately, the etiological factors behind the development of kidney disease in diabetics are not fully understood, although high blood pressure and high levels of blood glucose increase the risk that a person with diabetes will progress to kidney failure. Diagnostically, diabetics developing kidney disease can have small amounts of the blood protein albumin in the urine, a condition called microalbuminuria. This phenomenon increases as the disease progresses. Conventional quantitative methods for diagnosing kidney disease in diabetics measure the presence of serum albumin in urine, although with varying degrees of sensitivity, accuracy, and precision.

These assays include antibody-based methods such as radioimmunoassay (RIAs), enzyme-linked immunoassays (ELISAs), immunoturbidimetric assays, nephelometric assays, and non-antibody-based methods such as high performance liquid chromatography (HPLC). Additionally, semi-quantitative methods such as gold immunoassays, latex agglutination, silver dot blot assays, and nigrosin assays are also available. The antibody-based assays suffer from the limitation of "epitopic specificity." These assays have been developed primarily to detect and quantify urinary albumin and are capable of detecting and quantifying only those albumin moieties that bear antibody-specific epitopes. A fragment or peptide derived from an intact albumin molecule may not be detected by a particular albumin antibody-based assay if the urinary albumin peptide does not bear an epitope specific for the antibodies used in the immunoassays. The semi-quantitative methods of albumin detection are, generally speaking, not accurate and/or sensitive enough for the early detection of the onset of microalbuminuria.

Thus, there remains a need in the art for diagnostic methods for identifying individuals, most preferably diabetics, undergoing early onset, having, or at risk for developing kidney disease.

SUMMARY OF THE INVENTION

This invention provides reagents and methods for performing diagnostic assays for identifying animals, preferably humans, and more preferably humans with diabetes, who have or are at risk for developing kidney disease.

In a first aspect the invention provides methods for diagnosing kidney disease using urine from a diabetic animal. The inventive methods comprise the step of assaying a urine sample from a diabetic human or animal with an immunological reagent immunologically-specific for a protein or peptide differentially produced in urine from a diabetic having or at risk for developing kidney disease, wherein kidney disease is diagnosed when at least one said protein or peptide is detected. In preferred embodiments, the immunological reagents provided by the invention are polyclonal antisera, or one or a plurality of monoclonal antibodies immunologically specific for a protein or peptide differentially produced in urine from a diabetic having or at risk for developing kidney disease. Preferably, kidney diseases diagnosed using the methods of the invention include but are not limited to acute and chronic renal diseases such as diabetic nephropathy, glomerulonephritis, amyloidosis, IgA nephritis, congestive heart failure, cardiovascular disease, renal malignancies, and/or lower urinary tract infection. A most preferred subject for this assay is a human, preferably a human with diabetes. In preferred embodiments, said polyclonal antisera or monoclonal antibody do not immunologically cross-react with serum albumin.

In preferred embodiments, the immunological reagent is immunologically-specific for at least one urinary protein or peptide thereof that is zinc alpha-2-glycoptotein, alpha-1 microglobulin, alpha-1-acid glycoprotein 1, alpha-1-acid glycoprotein 2, IgG kappa chain (IGKV1-5), IgG lambda chain, prostaglandin-H2 D-isomerase precursor, HGFL protein, urine protein 1, complement regulatory protein CD59, thrombin, hemopexin, alpha-2-HS-glycoprotein precursor, G(M2)activator protein, pancreatic stone protein, saposin precursor, pepsin, kininogen, alpha-1B-glycoprotein, 90 kD protein, beta-trace 23 kD glycoprotein, haptoglobin, gelsolin, or whey acid protein. Preferably, the assay is an immunoassay, more preferably an enzyme-linked immunoassay. In preferred embodiments, the enzyme-linked immunoassay produces a detectable reaction product.

In alternative embodiments, the inventive methods of this aspect of the invention include the step of assaying said urine sample for serum albumin. In additional preferred embodiments, the assay is performed whereby the amount of said urinary protein or peptide is determined quantitatively, and wherein kidney disease is diagnosed when the amount of said urinary protein or peptide is detected in an amount higher than the amount detected in a urine sample from an animal without kidney disease.

In another aspect the invention provides methods for assessing a risk for developing kidney disease using urine from a diabetic animal. The inventive methods comprise the step of assaying a urine sample from a diabetic human or animal with an immunological reagent immunologically-specific for a protein or peptide differentially produced in urine from a diabetic having or at risk for developing kidney disease, wherein a risk for developing kidney disease is identified when at least one said protein or peptide is detected. In preferred embodiments, the immunological reagents provided by the invention are polyclonal antisera, or one or a plurality of monoclonal antibodies immunologically specific for a protein or peptide differentially produced in urine from a diabetic having or at risk for developing kidney disease. Preferably, a risk for developing kidney disease is identified when at least one said protein or peptide is detected using the methods of the invention. A most preferred subject for this assay is a human, preferably a human with diabetes. In preferred embodiments, said polyclonal antisera or monoclonal antibody does not immunologically cross-react with serum albumin.

In preferred embodiments, the immunological reagent is immunologically-specific for at least one urinary protein or peptide thereof that is zinc alpha-2-glycoptotein, alpha-1 microglobulin, alpha-1-acid glycoprotein 1, alpha-1-acid glycoprotein 2, IgG kappa chain (IGKV1-5), IgG lambda chain, prostaglandin-H2 D-isomerase precursor, HGFL protein, urine protein 1, complement regulatory protein CD59, thrombin, hemopexin, alpha-2-HS-glycoprotein precursor, G(M2)activator protein, pancreatic stone protein, saposin precursor, pepsin, kininogen, alpha-1B-glycoprotein, 90kD protein, beta-trace 23kD glycoprotein, haptoglobin, gelsolin, or whey acid protein. Preferably, the assay is an immunoassay, more preferably an enzyme-linked immunoassay. In preferred embodiments, the enzyme-linked immunoassay produces a detectable reaction product.

In alternative embodiments, the inventive methods of this aspect of the invention include the step of assaying said urine sample for serum albumin. In additional preferred embodiments, the assay is performed whereby the amount of said urinary protein or peptide is determined quantitatively, and wherein kidney disease is diagnosed when the amount of said urinary protein or peptide is detected in an amount higher than the amount detected in a urine sample from an animal without kidney disease.

The invention further provides a reagent that is a polyclonal antisera for diagnosing kidney disease in a human or animal. In this aspect, the polyclonal antisera comprises a plurality of antibodies immunologically specific for a protein or peptide differentially produced in urine from a diabetic having or at risk for developing kidney disease. In preferred embodiments, the polyclonal antisera of the invention does not immunologically cross-react with serum albumin. Preferably, the polyclonal antisera of the invention is immunologically-specific for at least one urinary protein or peptide thereof that is zinc alpha-2-glycoptotein, alpha-1 microglobulin, alpha-1-acid glycoprotein 1, alpha-1-acid glycoprotein 2, IgG kappa chain (IGKV1-5), IgG lambda chain, prostaglandin-H2 D-isomerase precursor, HGFL protein, urine protein 1, complement regulatory protein CD59, thrombin, hemopexin, alpha-2-HS-glycoprotein precursor, G(M2)activator protein, pancreatic stone protein, saposin precursor, pepsin, kininogen, alpha-1B-glycoprotein, 90kD protein, beta-trace 23kD glycoprotein, haptoglobin, gelsolin, or whey acid protein.

Preferred embodiments of the polyclonal antisera of this aspect of the invention are adapted for use in an immunoassay. Preferably, the immunoassay is an enzyme-linked immunoassay wherein the enzyme-linked immunoassay produces a detectable reaction product. Preferred polyclonal antisera are adapted for use in an assay that is performed whereby the amount of said urinary protein or peptide is determined quantitatively.

In another aspect, the invention further provides a diagnostic reagent comprising polyclonal antisera for diagnosing kidney disease in a human or animal. In this aspect, the diagnostic reagent comprises a plurality of antibodies immunologically specific for a protein or peptide differentially produced in urine from a diabetic having or at risk for developing kidney disease. In preferred embodiments, the diagnostic reagent of the invention does not immunologically cross-react with serum albumin. Preferably, the diagnostic reagent of the invention is immunologically-specific for at least one urinary protein or peptide thereof that is zinc alpha-2-glycoptotein, alpha-1 microglobulin, alpha-1-acid glycoprotein 1, alpha-1-acid glycoprotein 2, IgG kappa chain (IGKV1-5), IgG lambda chain, prostaglandin-H2 D-isomerase precursor, HGFL protein, urine protein 1, complement regulatory protein CD59, thrombin, hemopexin, alpha-2-HS-glycoprotein precursor, G(M2)activator protein, pancreatic stone protein, saposin precursor, pepsin, kininogen, alpha-1B-glycoprotein, 90kD protein, beta-trace 23kD glycoprotein, haptoglobin, gelsolin, or whey acid protein.

Preferred embodiments of the diagnostic reagents of the invention are adapted for use in an immunoassay. Preferably, the immunoassay is an enzyme-linked immunoassay wherein the enzyme-linked immunoassay produces a detectable reaction product. Preferred diagnostic reagents are adapted for use in an assay that is performed whereby the amount of said urinary protein or peptide is determined quantitatively.

In another aspect, the invention further provides a diagnostic reagent for diagnosing kidney disease in a human or animal comprising a plurality of monoclonal antibodies immunologically specific for a protein or peptide differentially produced in urine from a diabetic having or at risk for developing kidney disease. In this aspect, the plurality of monoclonal antibodies is immunologically specific for at lease one protein or peptide differentially produced in urine from a diabetic having or at risk for developing kidney disease. In preferred embodiments, the diagnostic reagent of the invention does not immunologically cross-react with serum albumin. Preferably, the diagnostic reagent of the invention is immunologically-specific for at least one urinary protein or peptide thereof that is zinc alpha-2-glycoptotein, alpha-1 microglobulin, alpha-1-acid glycoprotein 1, alpha-1-acid glycoprotein 2, IgG kappa chain (IGKV1-5), IgG lambda chain, prostaglandin-H2 D-isomerase precursor, HGFL protein, urine protein 1, complement regulatory protein CD59, thrombin, hemopexin, alpha-2-HS-glycoprotein precursor, G(M2)activator protein, pancreatic stone protein, saposin precursor, pepsin, kininogen, alpha-1B-glycoprotein, 90kD protein, beta-trace 23kD glycoprotein, haptoglobin, gelsolin, or whey acid protein.

Preferred embodiments of the diagnostic reagents of this aspect of the invention are adapted for use in an immunoassay. Preferably, the immunoassay is an enzyme-linked immunoassay wherein the enzyme-linked immunoassay produces a detectable reaction product. In preferred diagnostic reagents, at least one of the plurality of monoclonal antibodies is adapted for use in an assay that is performed whereby the amount of said urinary protein or peptide is determined quantitatively.

The invention also provides kits for performing the methods of the invention. In preferred embodiments, the kits of the invention comprise a diagnostic reagent of the invention. In alternative embodiments the kits of the invention further comprise a reagent for assaying serum albumin in a urine sample, preferably an immunological reagent. In preferred embodiments, the diagnostic reagents of the kits provided by the invention are adapted for use in an immunoassay, preferably an enzyme-linked immunoassay and more preferably wherein the enzyme-linked immunoassay produces a detectable reaction product. In certain embodiments, the diagnostic reagent comprises a polyclonal antisera. In other embodiments, the diagnostic reagent comprises a plurality of monoclonal antibodies immunologically specific for a protein or peptide differentially produced in urine from a diabetic having or at risk for developing kidney disease. In preferred embodiments of the inventive kits, the immunological reagents are adapted for use in an assay that is performed whereby the amount of said urinary protein or peptide is determined quantitatively. Preferably, polyclonal antisera or the plurality of monoclonal antibodies comprising the diagnostic reagents of the invention are immunologically-specific for at least one urinary protein or peptide thereof that is zinc alpha-2-glycoptotein, alpha-1 microglobulin, alpha-1-acid glycoprotein 1, alpha-1-acid glycoprotein 2, IgG kappa chain (IGKV1-5), IgG lambda chain, prostaglandin-H2 D-isomerase precursor, HGFL protein, urine protein 1, complement regulatory protein CD59, thrombin, hemopexin, alpha-2-HS-glycoprotein precursor, G(M2)activator protein, pancreatic stone protein, saposin precursor, pepsin, kininogen, alpha-1B-glycoprotein, 90kD protein, beta-trace 23kD glycoprotein, haptoglobin, gelsolin, or whey acid protein.

The invention also provides an antigenic mixture for producing a polyclonal antisera, or a plurality of monoclonal antibodies comprising at least one urinary protein or peptide thereof that is zinc alpha-2-glycoptotein, alpha-1 microglobulin, alpha-1-acid glycoprotein 1, alpha-1-acid glycoprotein 2, IgG kappa chain (IGKV1-5), IgG lambda chain, prostaglandin-H2 D-isomerase precursor, HGFL protein, urine protein 1, complement regulatory protein CD59, thrombin, hemopexin, alpha-2-HS-glycoprotein precursor, G(M2)activator protein, pancreatic stone protein, saposin precursor, pepsin, kininogen, alpha-1B-glycoprotein, 90kD protein, beta-trace 23kD glycoprotein, haptoglobin, gelsolin, or whey acid protein.

The inventive methods are advantageous over methods known in the art. The combined use of a urinary protein ELISA and a urinary albumin measurement (performed by either immunoassay or nephelometry) is a significant improvement over existing diagnostic measurements in terms of higher sample analytical throughput and improved sensitivity for the early detection of microalbuminuria. Greater assay sensitivity leading to the earlier detection of kidney dysfunction will promote earlier medical intervention and reduce disease morbidity.

Specific embodiments of the present invention will become evident from the following more detailed description of certain preferred embodiments and the claims.

BRIEF DESCRIPTION OF THE DRAWINGS

FIG. 5 shows the results of liquid chromatography-mass spectrometry analysis of a purified urinary protein preparations.

FIG. 7 shows the relative abundance of specific urinary proteins or peptides in the urinary protein preparation as determined by LC-MS/MS.

FIG. 13 shows representative standard curves from competitive immunoassays for the quantitation of HSA and human urinary proteins.

FIG. 16 shows a correlation between the urinary protein (GA) ELISA methods described herein and an art-recognized HPLC reference method.

DETAILED DESCRIPTION OF THE PREFERRED EMBODIMENTS

Figure 1:
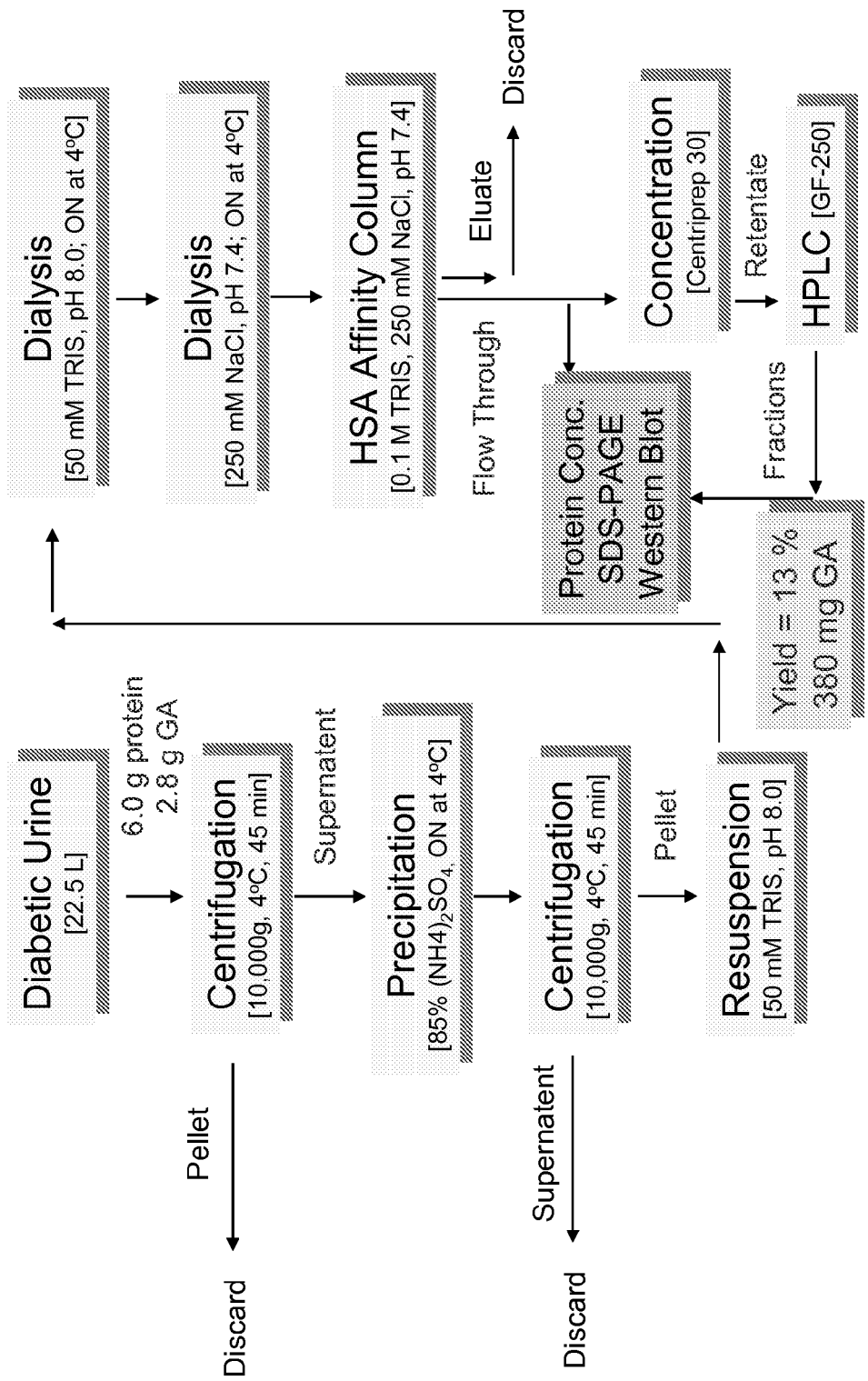
FIG. 1 is a schematic diagram of a protocol for the purification of urinary proteins/peptides from human diabetic urine.

The invention provides antibodies that are immunologically reactive to a plurality of urinary proteins and peptides, preferably human urinary proteins and peptides, and even more preferably human urinary proteins and peptides in urine from a human with diabetes. The antibodies provided by the invention can be raised in animals by inoculation with protein and/or peptide isolates from urine, preferably human urine and even more preferably urine from a human with diabetes, using methods well known in the art. (See, Harlow et al., 1988, ANTIBODIES: A LABORATORY APPROACH, Cold Spring Harbor Laboratory New York) Animals that can be used for such inoculations include individuals from species comprising cows, sheep, pigs, mice, rats, rabbits, hamsters, goats and primates. Preferred animals for inoculation are sheep, goats, rodents (including mice, rats, hamsters) and rabbits.

Protein and/or peptide isolates from urine, preferably human urine and more preferably human diabetic urine, can be obtained from urine samples using biochemical fractionation methods. In preferred embodiments, said isolates are treated to be depleted in, and preferably be substantially without contamination by, serum albumin, particularly human serum albumin. Methods for reducing or removing serum albumin from protein/peptide urinary isolates include but are not limited to differential precipitation, size exclusion chromatography, ion exchange chromatography, and preferably affinity chromatography using serum albumin-specific binding agents. Non-chromatographic embodiments of such affinity methods also fall within the scope of this aspect of the invention.

The present invention also provides monoclonal antibodies that are immunologically reactive with an epitope that comprises a protein or peptide in urine, preferably human urine and more preferably urine from a human with diabetes. Said monoclonal antibodies are made using methods and techniques well known to those of skill in the art. (See, Harlow et al., ibid.) Monoclonal antibodies provided by the present invention are produced by hybridoma cell lines, that are also provided by the invention and that are made by methods well known in the art. Id. Generally, hybridoma cell lines are made by fusing individual cells of a myeloma cell line with spleen cells derived from animals immunized with a plurality of proteins/peptides from urine, preferably human urine and more preferably urine from a human with diabetes. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. Preferred animals from whom spleens are obtained after immunization are rats, mice and hamsters, preferably mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention can also be produced by recombinant genetic methods well known to those of skill in the art, and the present invention encompasses antibodies made by such methods that are immunologically reactive with an epitope of a protein or peptide comprising urine, preferably human urine and more preferably urine from a human with diabetes.

The present invention also encompasses fragments of the antibody that are immunologically reactive with an epitope of a protein or peptide comprising urine, preferably human urine and more preferably urine from a human with diabetes. Such fragments, including F(ab), F(ab)$_2$, F(ab)' and F$_v$ fragments, can be produced by any number of methods, including but not limited to proteolytic cleavage, chemical synthesis or preparation of such fragments by means of genetic engineering technology. The present invention also encompasses single-chain antibodies that are immunologically reactive with an epitope of a protein or peptide comprising urine, preferably human urine and more preferably urine from a human with diabetes made by methods known to those of skill in the art.

The invention also includes chimeric antibodies, comprised of immunologically reactive light chain and heavy chain peptides to an epitope of a protein or peptide comprising urine, preferably human urine and more preferably urine from a human with diabetes. The chimeric antibodies embodied in the present invention include those that are derived from naturally occurring antibodies as well as chimeric antibodies made by means of genetic engineering technology well known to those of skill in the art.

For the purposes of this invention, the term "immunological reagents" is intended to encompass polyclonal antisera and antibodies, particularly monoclonal antibodies, as well as fragments thereof (including F(ab), F(ab)$_2$, F(ab)' and F$_v$ fragments). Also included in the definition of immunological reagent are chimeric antibodies, humanized antibodies, and recombinantly-produced antibodies and fragments thereof. In particular, immunological reagents of this invention are immunologically specific for urinary proteins, most preferably human urinary proteins, produced in urine from a diabetic individual that has or is at risk for developing kidney disease.

Immunological methods used in conjunction with the reagents of the invention include direct and indirect (for example, sandwich-type) labeling techniques, immunoaffinity columns, immunomagnetic beads, polystyrene or agarose beads, fluorescence activated cell sorting (FACS), enzyme-linked immunosorbent assays (ELISA), and radioimmune assay (RIA). For use in these assays, the urinary protein- and peptide-specific immunological reagents of this invention can be labeled, using fluorescence, luminescent, antigenic, radioisotopic, or biotin labels, or more preferably enzymatically-labeled, wherein immunospecific binding can be detected by incubation with a cognate substrate of said enzyme. Most preferably, enzymatic activity converts said substrate into a detectable product, or alternatively reduces the amount of a detectable substrate. In preferred embodiments, the detectable product is a colored product. Alternatively, the claimed immunological reagents, advantageously as polyclonal antisera embodiments thereof, can be used in conjunction with labeled secondary immunological detection reagents, for example in secondary antibody (sandwich) assays. In these aspects, labeled antibodies or antisera can be used that are immunologically-specific and reactive against the immunological reagents specific and reactive against urinary proteins and peptides. Examples of said primary/secondary immunological reagents include, inter alia, sheep anti-human urinary protein/peptide primary antibodies and rabbit (or other mammalian species) anti-sheep immunoglobulin antisera. Monoclonal antibody embodiments of either primary or secondary antibodies or both also fall with the scope of these embodiments of the invention.

Particularly useful embodiments of the present invention and the advantages thereof can be understood by referring to the following Examples. These Examples are illustrative of specific embodiments of the invention, and various uses thereof. They are set forth for explanatory purposes only, and are not to be taken as limiting the invention.

EXAMPLES

Figure 12:
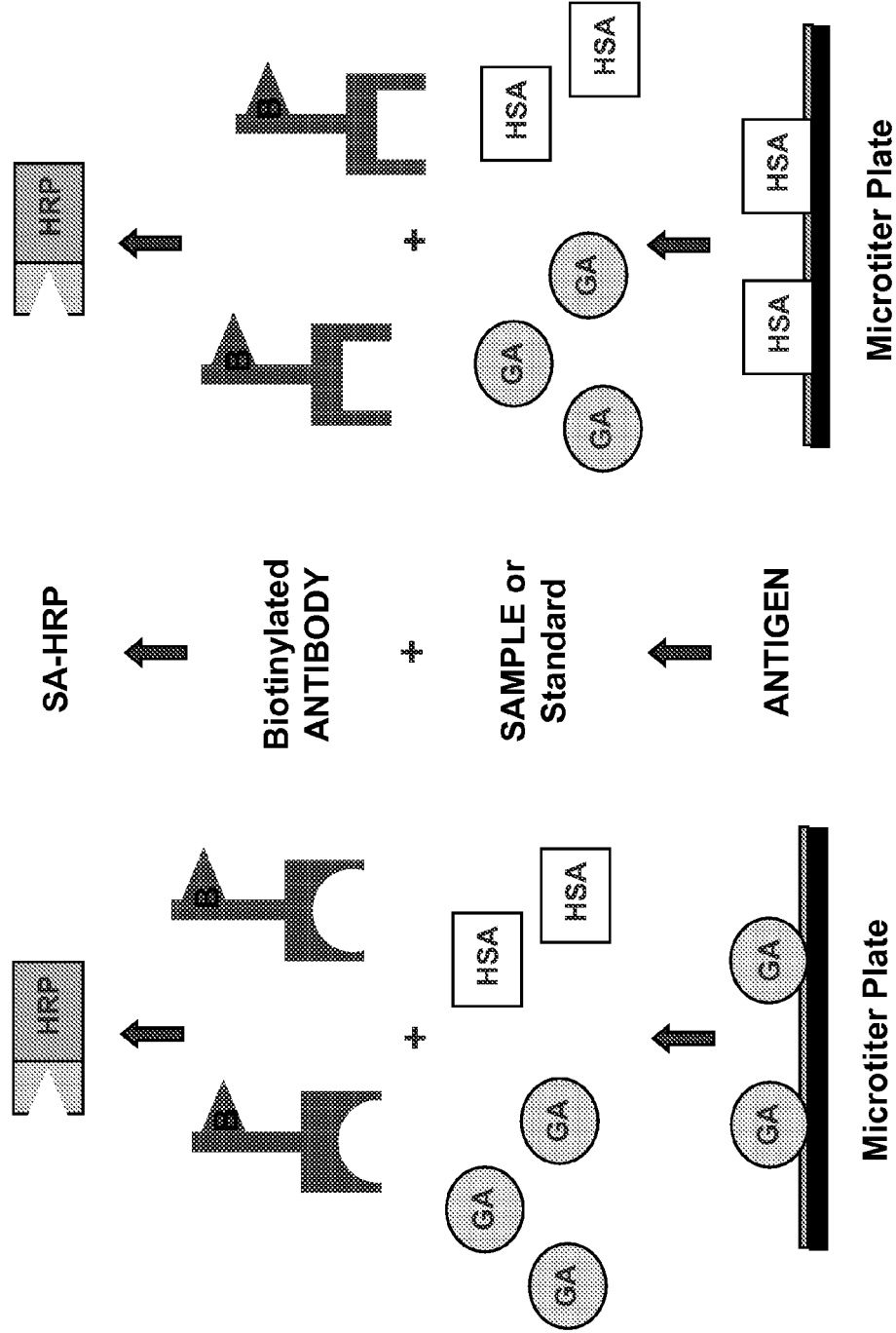
FIG. 12 is a schematic diagram of the competitive immunoassay protocols for the quantitation of urinary proteins and HSA, wherein GA are urinary proteins; HSA is human serum albumin; HRP is horseradish peroxidase; and B is biotin.

ELISA Assay Protocol
Competitive immunoassays were performed as follows and as shown in FIG. 12 Immulon-4 HBX plates (Thermo Lab Systems; Franklin, Mass.) were coated with 100μL of a 0.1M sodium borate solution containing either 0.05μg/mL HSA or 0.5μg/mL GA and incubated for 1 h at 37° C. with gentle shaking. After incubation excess reagent was removed by washing the plate three times with PBS containing 0.005% Tween 80. Prior to use, the plates were blocked (to prevent non-specific binding) using 150μL PBS containing 0.005% Tween 80 and 0.5mg/mL ovalbumin. The plates were then incubated for 1h at 37° C. with gentle shaking, and excess reagent again removed by washing the plate three times with PBS containing 0.005% Tween 80.

For the assay, 50μL PBS containing 0.005% Tween 80 was added to each plate, and then 25μL of a 1:12.5 dilution of sample in PBS/0.005% Tween 80 in triplicate were added. In parallel, a standard curve was constructed by adding 25μL of a three-fold serially diluted concentration of HSA or urinary protein standard to each of three wells (A1-3 to H1-3); standard curves for GA and HSA are shown in FIG. 13. The clinical relevant range for the measurement of urinary albuminuria (2μg/mL to 200μg/mL) is indicated. Primary antibody binding was detected by adding 25μL of either biotinylated HSA secondary antibody (at a concentration of 0.1 μg/mL, equal to 0.025μg/mL) or 25μL of biotinylated GA secondary antibody (at a concentration of 0.133μg/mL, equal to 0.033μg/mL), followed by incubation at room temperature for 1h with gentle shaking. After secondary antibody incubation, the plates were washed three times with PBS containing 0.005% Tween 80.

Secondary antibody binding was detected by adding 100 μL PBS containing 0.005% Tween 80 and a 1:25,000 dilution of streptavidin conjugated with horseradish peroxidase (Sigma Chemical Co., St. Louis, Mo.) and incubated for 1 h at room temperature with gentle shaking. Excess reagent was removed by washing the plates five times with PBS containing 0.005% Tween 80. Finally, 75 μL tetramethylbenzidine (TMB) was added to each plate and the plates shaken at room temperature for 10 min, followed by the addition of 150 μL of 1M sulfuric acid, which was mixed and the assay mixture evaluated by spectroscopy at 450 nm.

Example 1

Urinary Protein and Peptide Isolation

Urinary proteins and peptides were isolated as follows. Urine from a diabetic individual (22.5 L containing approximately 6 g protein and 2.8 g of non-albumin urinary proteins (GA) was subjected to centrifugation for 45 min at 4° C. and 10,000×g. The pellet was discarded and ammonium sulfate added to a final concentration of 85% w/v, and then kept overnight at 4° C. This mixture was then centrifuged for 45 min at 4° C. and 10,000×g and the protein and peptide-containing pellet recovered and resuspended in a solution of 50mM Tris buffer (pH 8.0). Dissolved ammonium sulfate was removed from the resuspended protein/peptide solution by dialysis against an excess of a solution of 50mM Tris buffer (pH 8.0) overnight at 4° C., followed by further dialysis against an excess of a solution of 250mM NaCl (pH 7.4) overnight at 4° C. The resulting protein and peptide-containing solution was passed over a human serum albumin (HSA) affinity column using a solution of 0.1M Tris, 250nM NaCl (pH 7.4). The flow-through was collected and HSA eluted from the column was discarded. The flow-through was concentrated using a Centriprep 30 column (Amicon, Beverly, Mass., CA# 4306) according to the manufacturer's instructions. The concentrated retentate was fractionated by high pressure liquid chromatography using a DuPont Bioseries GF-250 size exclusion column (9.4×250 mm), and individual peak fractions collected. The overall yield was estimated to be about 13%, based on a yield of 380 mg of urinary proteins. This isolation protocol is illustrated schematically in FIG. 1.

Figure 2:
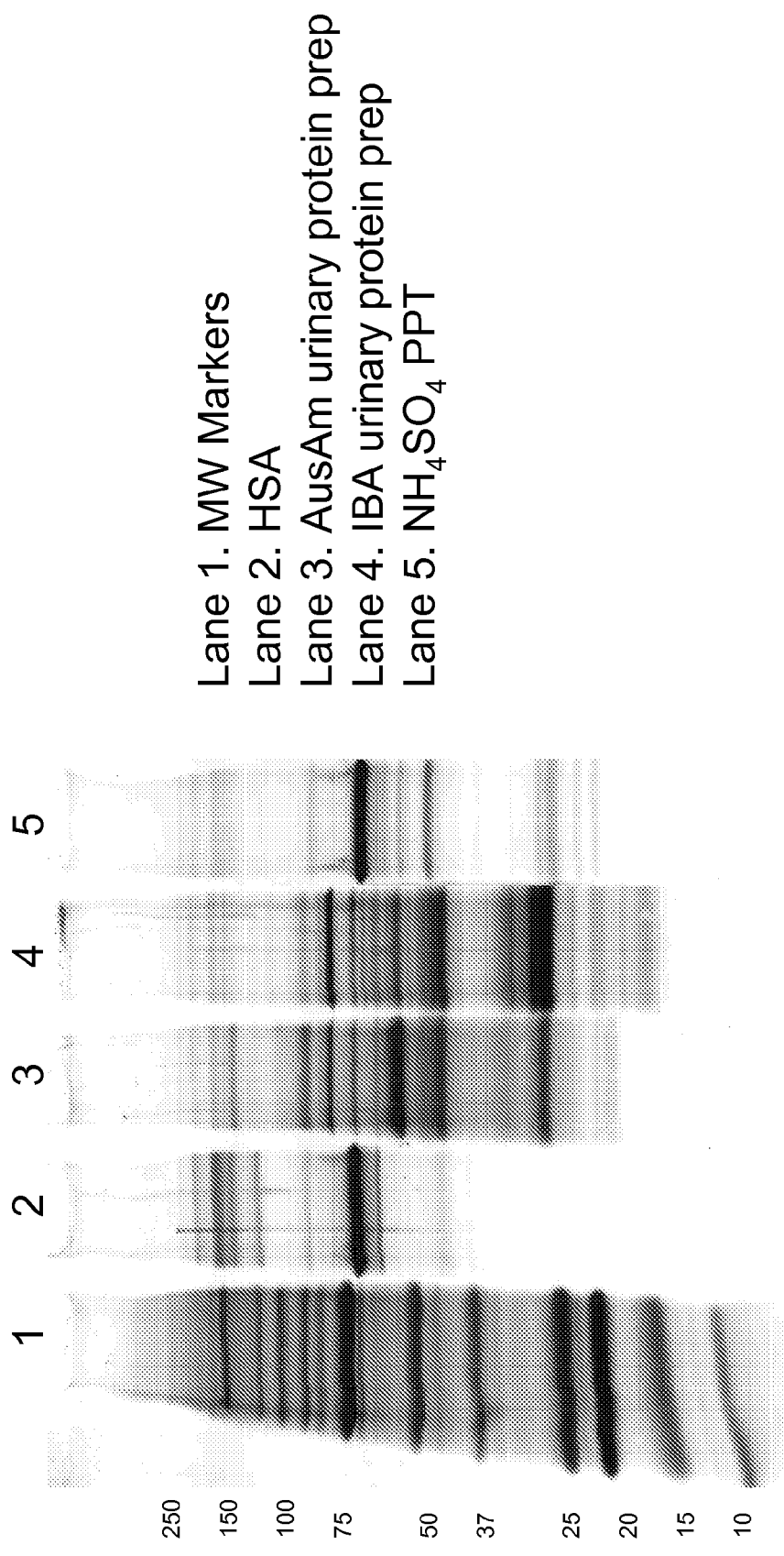
FIG. 2 is a photograph of a denaturing polyacrylamide gel showing biochemical analysis of urinary proteins. At various stages during the purification process, purified preparations were subjected to denaturing SDS-polyacrylamide gel electrophoresis (SDS-PAGE) in a 6% acrylamide gel using conventional techniques (Laemmli, 1970, Nature 227: 680-685). Lane 1 contains molecular weight markers; Lane 2, human serum albumin (HSA); Lanes 3 and 4, purified urinary protein preparations; and Lane 5, an ammonium sulfate precipitate fraction.

Fractions obtained from HPLC were concentrated and analyzed by SDS-PAGE and Western blotting using conventional techniques (Laemmli, 1970. *Nature* 227: 680-685). SDS-PAGE results are shown in FIG. 2, which are visualized using a non-specific colloidal gold protein stain. Comparison of the proteins detected in Lane 5, which was a sample of the dialysed ammonium sulfate precipitate, and Lane 4, which was a sample of the final protein/peptide isolate, and Lane 2, which is a purified HSA standard, showed that the predominant protein comprising the precipitate was HSA, which was substantially removed by HSA affinity chromatography. Comparison of Lanes 3 and 4 shows that the results obtained using the method set forth herein are substantially similar to results obtained using an alternative method (AusAm) known in the art, at least qualitatively, while revealing quantitative differences in the relative amounts of certain proteins (shown by more intense staining/broader band cross-sectional area). It will be appreciated that, due to the non-specificity of the staining it cannot be determine whether these quantitative differences are due to differentially higher yield of any particular protein or peptide species.

Figure 3:
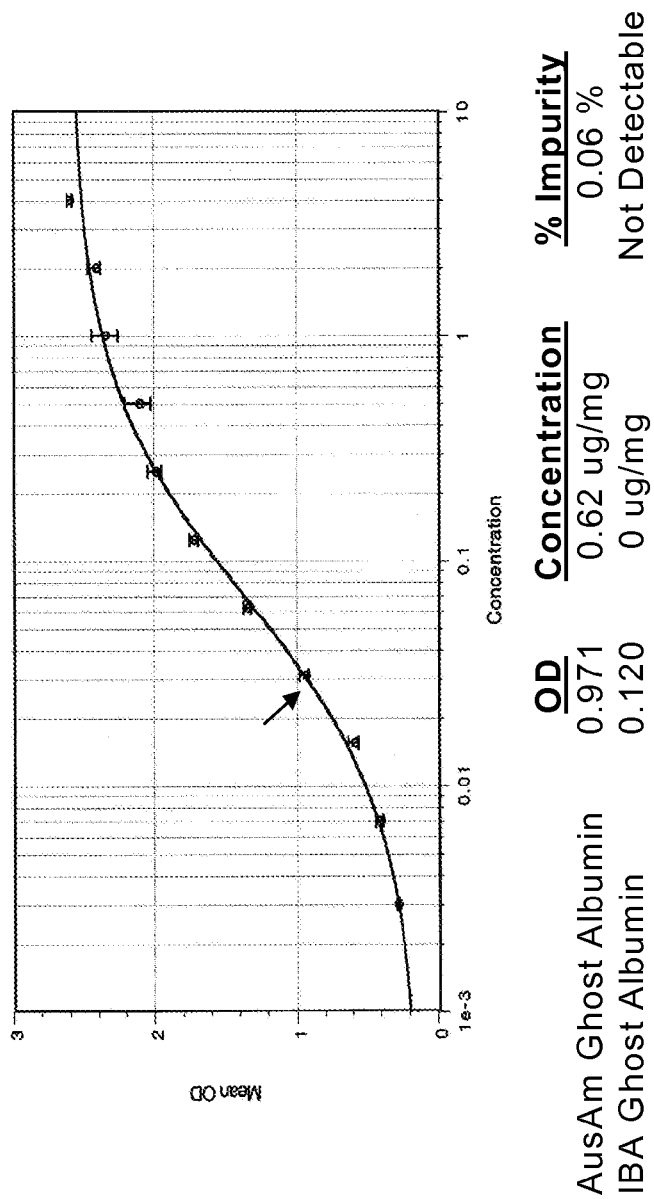
FIG. 3 shows a standard curve from a commercially-available ELISA assay for HSA used to quantitate the amount of residual human serum albumin (HSA) in urinary protein preparations. The arrow indicates the concentration of HSA observed in one of the urinary protein preparations.

The amount of residual HSA in the unfractionated protein/peptide isolate was assessed by enzyme-linked immunoassay (ELISA) using a commercially-available ELISA kit containing an anti-HSA antibody (Alpha Diagnostics International, San Antonio, Tex.). FIG. 3 shows the standard curve used with this assay, and the arrow shows the point on the curve indicating the amount of residual HSA detected in one urinary protein/peptide preparation (the AusAm alternative method) that was not detected using the methods as set forth herein. Comparison with the results obtained using the alternative AusAm method show that the methods of this invention contain undetectable amounts of residual HSA, while the art-recognized methods contain about 0.06% residual HSA by weight.

Figure 4:
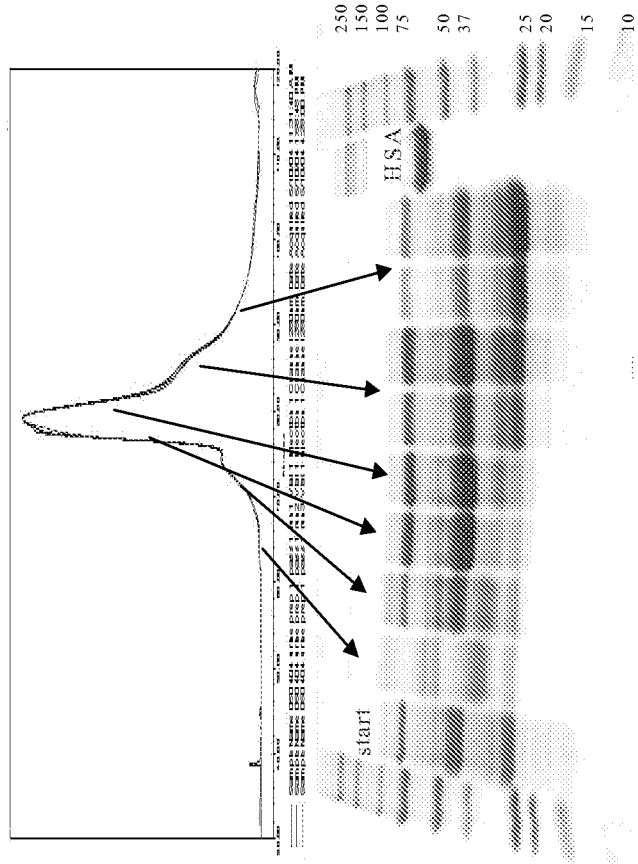
FIG. 4 show the results of gel filtration analysis of a urinary protein preparation. Arrows indicate the gel filtration fractions and their corresponding electrophoretic profiles. Molecular weight markers are shown in Lanes 1 and 12, indicated in units of kDa. Unpurified starting material (start) that was applied to the column was analyzed in Lane 2. Purified HSA was run in Lane 11. No endogenous HSA bands were observed in any of the urinary protein column fractions (Lanes 3 through 10).

These results were confirmed by SDS-PAGE analysis of HPLC-fractionated urinary protein/peptide preparations. As part of the urinary protein purification process set forth above, urinary protein preparations were purified over a GF-250 HPLC gel filtration column. Fractions were collected and subjected to SDS-PAGE on a 6% acrylamide gel using a standard electrophoresis protocol. These results are shown in FIG. 4, stained with Coomassie blue, a non-specific protein stain, with the results of a scan for staining intensity shown above. Lane 2 shows the unfractionated isolate (start), and Lane 11 shows purified HSA. As can be seen from the Figure, HSA is substantially absent from the unfractionated isolate, and is not detected in any of the isolated fractions (which was expected to reveal any residual HSA present at too low a concentration to be detectable in the unfractionated isolate)

Thus, these results indicate that preparations made using the instant methods are advantageous over the art-recognized methods, inter alia, for the production of polyclonal antisera and monoclonal antibodies against these urinary proteins, since it would be less likely to raise anti-HSA antibodies.

Example 2

Urinary Protein and Peptide Analysis

To identify specific urinary proteins comprising the protein/peptide isolate prepared according to the methods set forth in Example 1, samples of the isolate were analyzed by liquid chromatography-mass spectrometry (LC-MS/MS). Isolate samples were first digested with trypsin and then subjected to LC-MS/MS (Hellman et al., 1995, *Anal Biochem.* 224: 451-455).

The results of two separate iterations of these experiments on the same urinary protein/peptide isolate are shown in FIG. 5. Proteins identified by this analysis are set forth with regard to the number of peptides from each protein detected. Although not quantitative, the relative amount of each identified protein in the urinary protein preparation can be estimated based on the number of peptides, derived from that particular protein, identified in the preparation. Notably, independent LC-MS/MS analyses of the trypsin-digested urinary protein/peptide preparation identified similar proteins in approximately similar concentrations.

These isolates were also analyzed by native (i.e., not denaturing) gel electrophoresis with and without preabsorption of transferrin (Tfr) and immunoglobulin (IgG) to remove these species of non-albumin urinary proteins. To remove these major non-albumin proteins (Trf and IgG) from the urinary protein preparation, the preparation was sequentially passed over anti-Trf and anti-IgG affinity columns using standard affinity chromatographic methods well known to those of skill in the art. The resulting eluate fractions were then subjected to native PAGE in a 12% polyacrylamide gel using conventional techniques (Fairbanks et al., 1971, *Biochem.* 10: 2607-2617). Gels were stained with Coomassie blue and photographed, and then were blotted onto a PVDF membrane using conventional Western blotting protocols (Towbin et al., 1979. *PNAS USA* 76: 4350-4354). The Western blots were also stained with Coomassie Blue.

Figure 6:
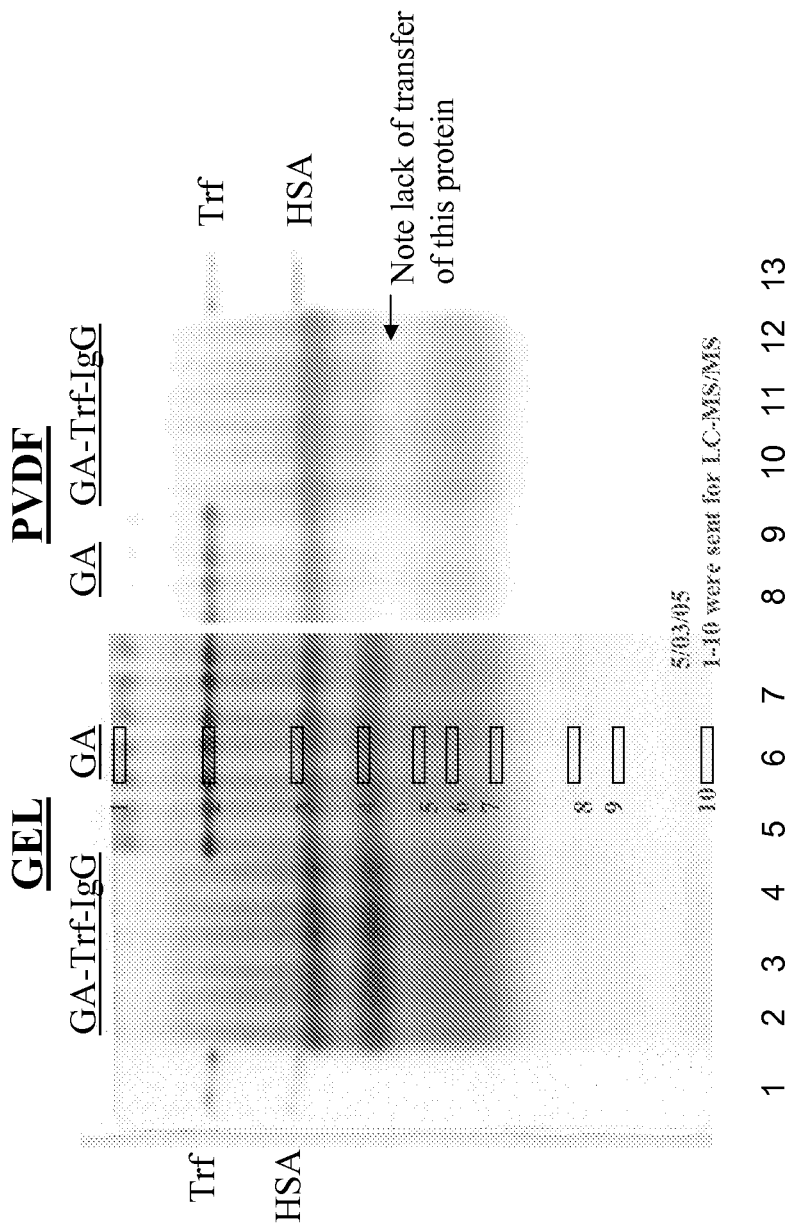
FIG. 6 shows the results of native PAGE and PVDF Western Blot of an untreated and transferrin (Trf) and immunoglobulin (IgG) absorbed urinary protein preparations.

The results of both native PAGE and Western blot analysis are shown in FIG. 6. In the Figure, lanes 1 and 13 were loaded with purified Trf and HSA standards; lanes 2-4, Trf and IgG absorbed urinary protein preparation; lanes 5-7, unabsorbed urinary protein preparations; Lanes 8 and 9, unabsorbed urinary protein preparation; lanes 10-12, Trf and IgG absorbed urinary protein preparation. Certain regions of the gel corresponding to stained protein bands were excised (locations indicated as 1-10) and further analyzed by LC-MS/MS as described above.

The results of LC-MS/MS analysis of these gel electrophoresis-resolved fractionated proteins are shown in FIG. 7. The preparation of purified urinary proteins was passed over Trf and IgG affinity columns and digested with trypsin. The molecular weights of the resultant peptides were identified by LC-MS/MS. This analysis was performed in duplicate utilizing the same urinary protein preparation. The results of both analyses are presented. The number of peptides observed and the relative "score" for each identified protein is presented. These results showed that repeat analysis of the same sample in two experiments gave similar albeit not identical data. The lower abundance proteins with 1 or 2 peptide matches tend to be found one time and not the next but the more abundant proteins seem to give more reproducible results. This is shown most notably by HSA, which was not detected in one experiment but was detected as 2 peptides at the very limit of the assay's sensitivity.

Example 3

Polyclonal Antibodies Against Urinary Protein and Peptides

Figure 8:
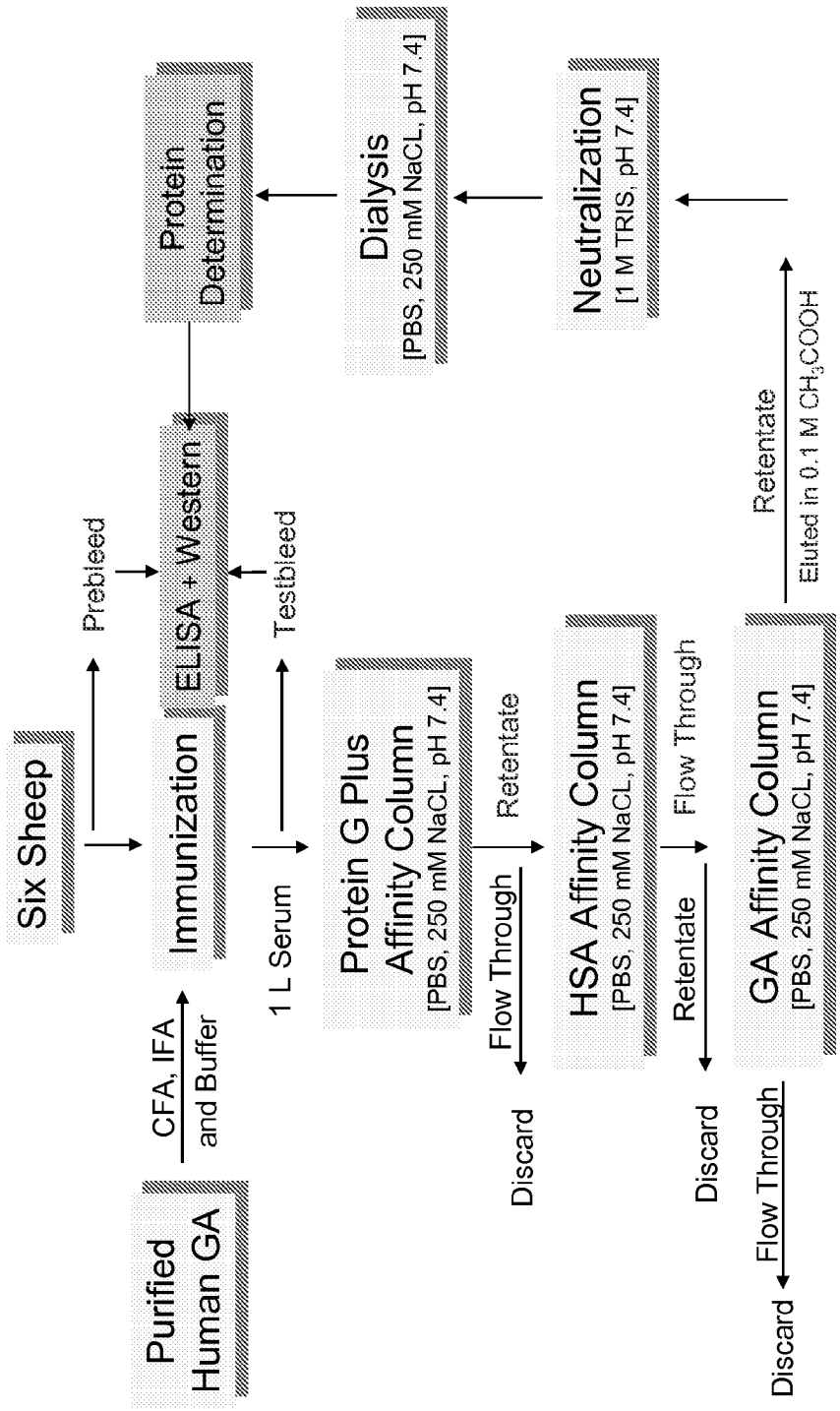
FIG. 8 is a schematic diagram of a protocol for the production and purification of sheep polyclonal antibodies to human urinary proteins.

Sheep polyclonal antibodies were raised against the urinary proteins and peptides isolated as set forth above. The protocol used for these experiments is shown in FIG. 8. Six sheep were sequentially immunized with purified human urinary proteins in CFA, IFA, and buffer. The sheep were testbled and the amount and specificity of anti-urinary protein antibodies present in their sera was determined by ELISA and Western blot employing protocols specified above. All immunized animals developed a high titer of specific urinary protein binding activity relative to their pre-immunization testbleeds. In sheep showing a productive immunological response, 1 L of high-titered animal sera was obtained and passed through a Protein G affinity column employing a standard protocol known to those schooled in the art. The flowthrough fraction was discarded and the polyclonal antisera fraction was eluted with 0.1 M acetic acid. This eluate was then passed through a HSA affinity column (to remove HSA specific antibodies) using PBS (pH 7.4) containing 250mM NaCl. The flowthrough was then passed through a urinary protein (GA) affinity column and the flowthrough discarded. The retentate was eluted with 0.1M acetic acid, neutralized with 1M Tris buffer, pH 7.4, dialyzed against an excess of PBS (pH 7.4) containing 250mM NaCl. Polyclonal anti-urinary protein antisera were biochemically and immunologically characterized by ELISA and Western blot employing protocols specified above.

Figure 9:
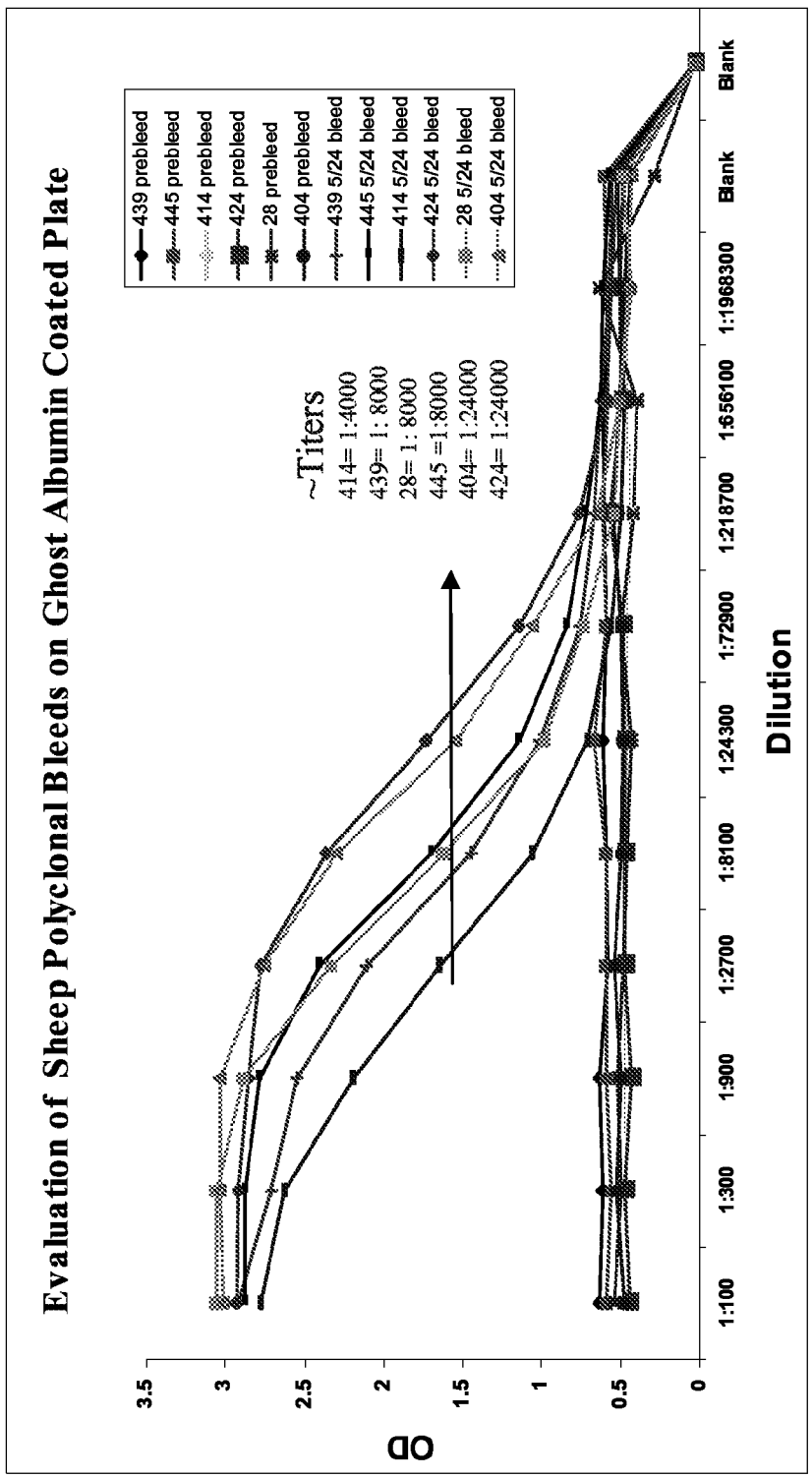
FIG. 9 is a graph of anti-urinary protein antibody titers from sheep antisera produced after sequential immunization with human urinary proteins.
Figure 10:
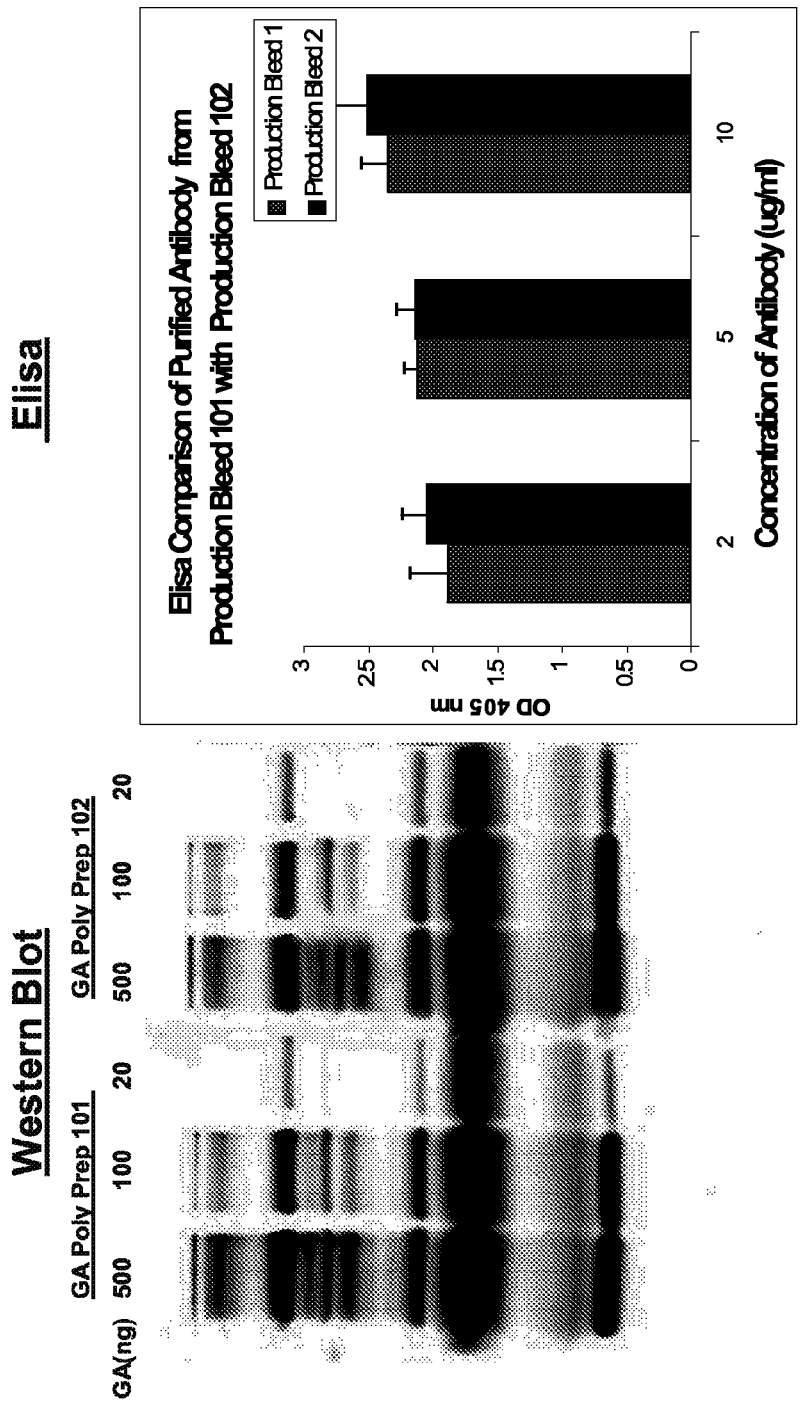
FIG. 10 shows the results of Western blot and ELISA analysis of anti-urinary protein antibodies.

Titers of various polyclonal antisera obtained from different experimental animals were determined by ELISA and the results shown in FIG. 9. These polyclonal antisera preparations were further characterized by Western blot and ELISA analyses, the results of which are shown in FIG. 10. Two different preparations of polyclonal antibodies (two production bleeds) were analyzed by Western blot and by direct-binding ELISA using a urinary protein coated microtiter plate. For Western blot analysis, various concentrations of urinary proteins were electrophoresed in 6% acrylamide gels, blotted onto PVDF membranes, and probed with purified sheep anti-urinary protein polyclonal antibodies from each production bleed. Both production bleeds of antibodies demonstrated identical urinary protein reactivity in the ELISA and Western blot, suggesting that antigenic reactivity across production bleeds and antigenic preparations lots were reproducible.

Figure 11:
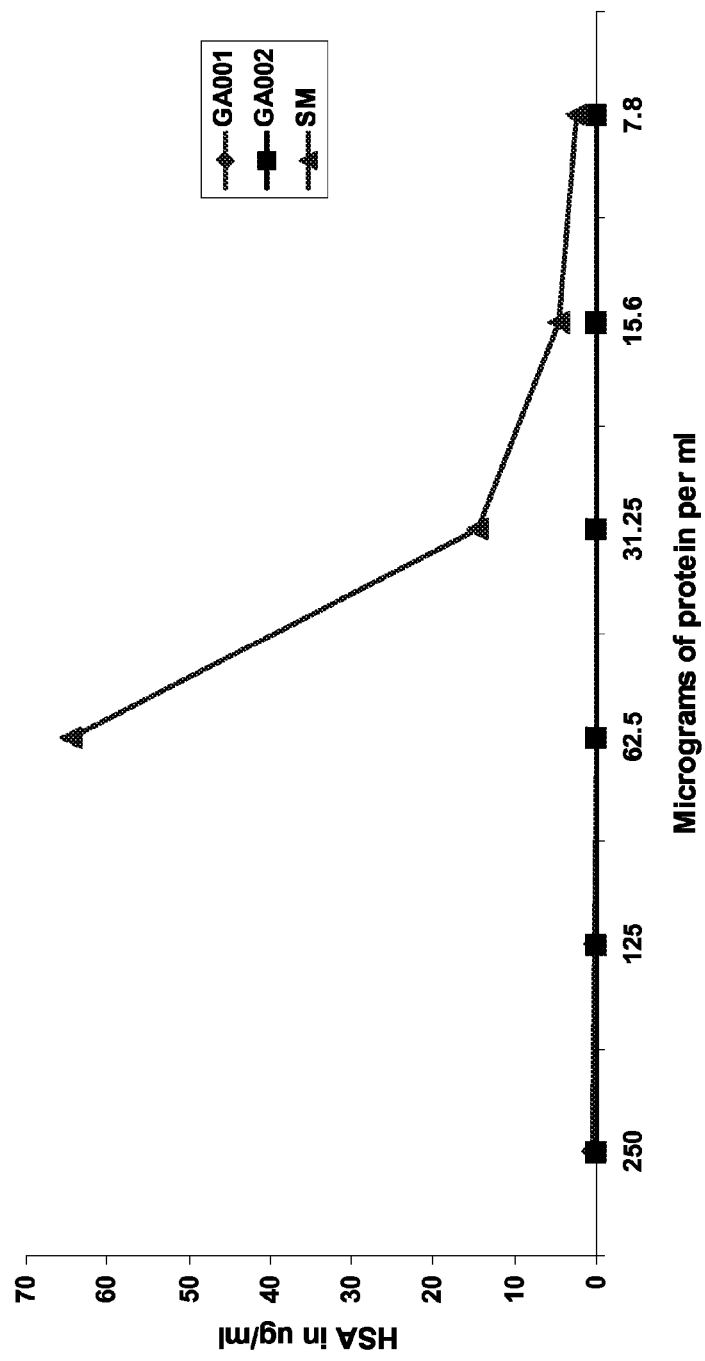
FIG. 11 is a graph showing removal of HSA reactivity of polyclonal anti-urinary protein antibody preparations.

Antisera from the same production bleeds were treated to remove HSA-reactive antibodies. After passage of partially purified antibody preparations over an HSA affinity column, the preparations were tested in a direct-binding ELISA to demonstrate complete removal of anti-HSA activity. These results are shown in FIG. 11. Both production lots of polyclonal antibodies showed complete remove of anti-HSA binding activity relative to the pre-HSA column passed starting material (SM).

Figure 14:
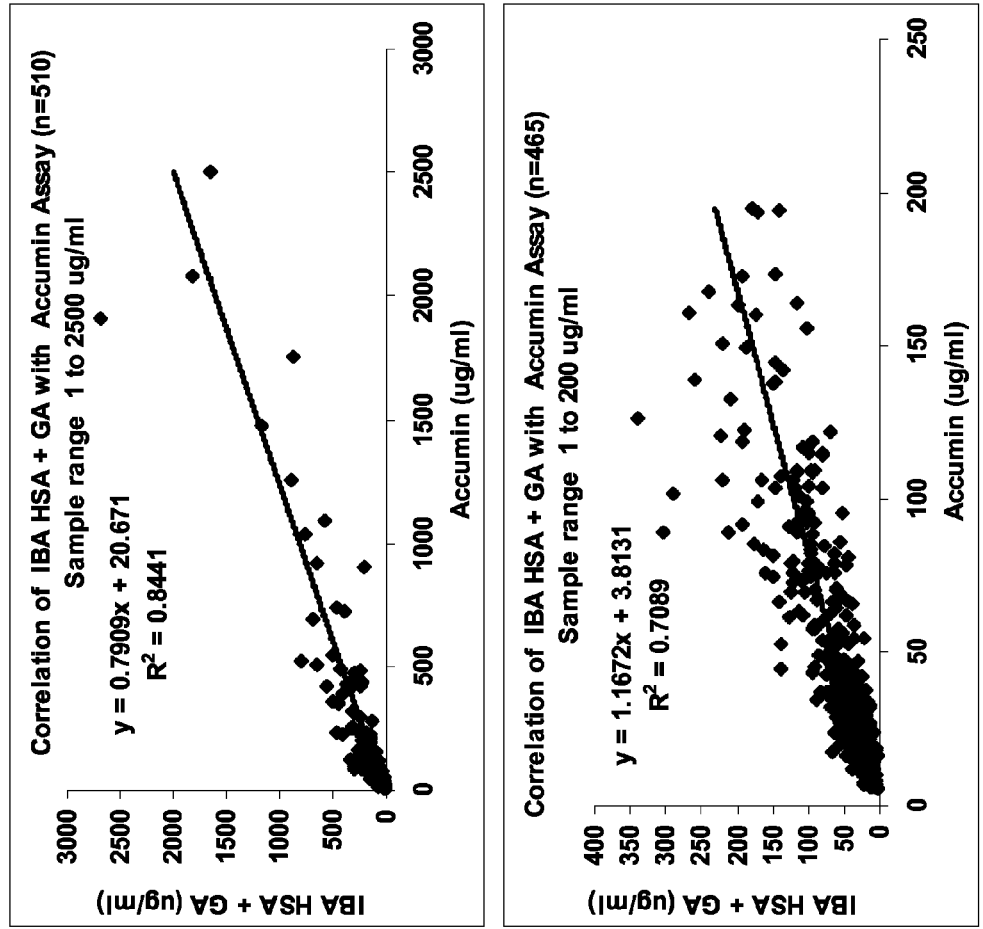
FIG. 14 are graphs showing correlation of HSA and urinary protein measurements with Accumin HPLC results. Top figure, correlation of HSA plus urinary protein ELISA results versus Accumin HPLC results in 510 normal and diabetic urine specimens. Bottom figure, correlation of HSA plus urinary protein ELISA results versus Accumin HPLC results in 465 normal and diabetic urine Specimens with albumin concentrations in the range of 1 to 200 ug/ml as determined by HPLC. The results demonstrate excellent correlation between the ELISAs and HPLC values.

The combined results of the HSA ELISA and the urinary protein (GA) ELISA, tested as set forth herein, were compared with an art-recognized immunoassay reference method (the AusAm method), as shown in FIG. 14. As shown in the top graph, the first comparison set comprised 510 normal and diabetic urine specimens, while the bottom graph shows the results of a second comparison employing a smaller subset of the initial test population (465 normal and diabetic urine specimens). In this subset of clinical specimens, all samples contained urinary albumin concentrations of 1 to 200 µg/mL (as measured by the AusAm assay). The results demonstrated good correlation between the combined HSA and urinary protein ELISA results and Accumin™ HPLC results.

Figure 15:
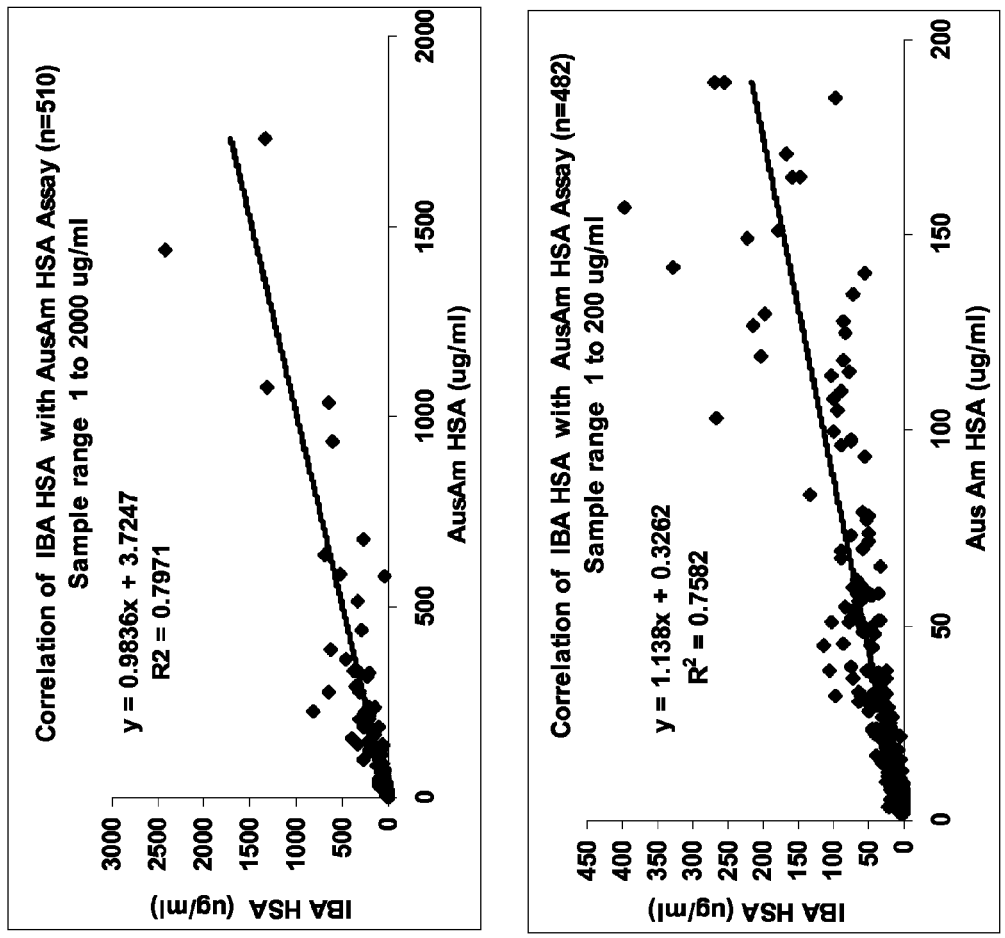
FIG. 15 shows a correlation between the HSA ELISA methods described herein and an art-recognized immunoassay reference method.

The HSA ELISA tested as set forth herein was also compared with an art-recognized immunoassay reference method (the AusAm method), as shown in FIG. 15. As shown in the top graph, the first comparison set comprised 510 normal and diabetic urine specimens, while the bottom graph shows the results of a second comparison, which had a comparison set of 465 normal and diabetic urine specimens; all in the range of 1 to 200 µg/mL of albumin (as measured by the AusAm assay). The results demonstrated good correlation between the sample albumin concentrations determined using the two ELISA methods.

The urinary protein ELISA tested as set forth herein was also compared with an art-recognized and FDA-approved HPLC reference method (Accumin™), as shown in FIG. 16. As shown in the top graph, the first comparison set comprised 510 normal and diabetic urine specimens, while the bottom graph shows the results of a second comparison, which had a comparison set of 465 normal and diabetic urine specimens; all in the range of 1 to 200 µg/mL. The observed poor correlation between the different methods suggested that the two methods were measuring different urinary proteins, further supporting the specificity of the polyclonal antisera as provided herein.

The ELISA assays provided herein were also analyzed for the accuracy of analyte quantitation. In these experiments, six urine samples were spiked with three different concentrations of HSA or urinary proteins and were then analyzed for HSA or urinary proteins levels using the appropriate ELISA. Recovery of either analyte at all concentrations of spiked analyte tested ranged from 80 to 108%, indicating excellent accuracy in HSA and urinary protein quantitation. These results are shown in Table 1 below.

Figure 17:
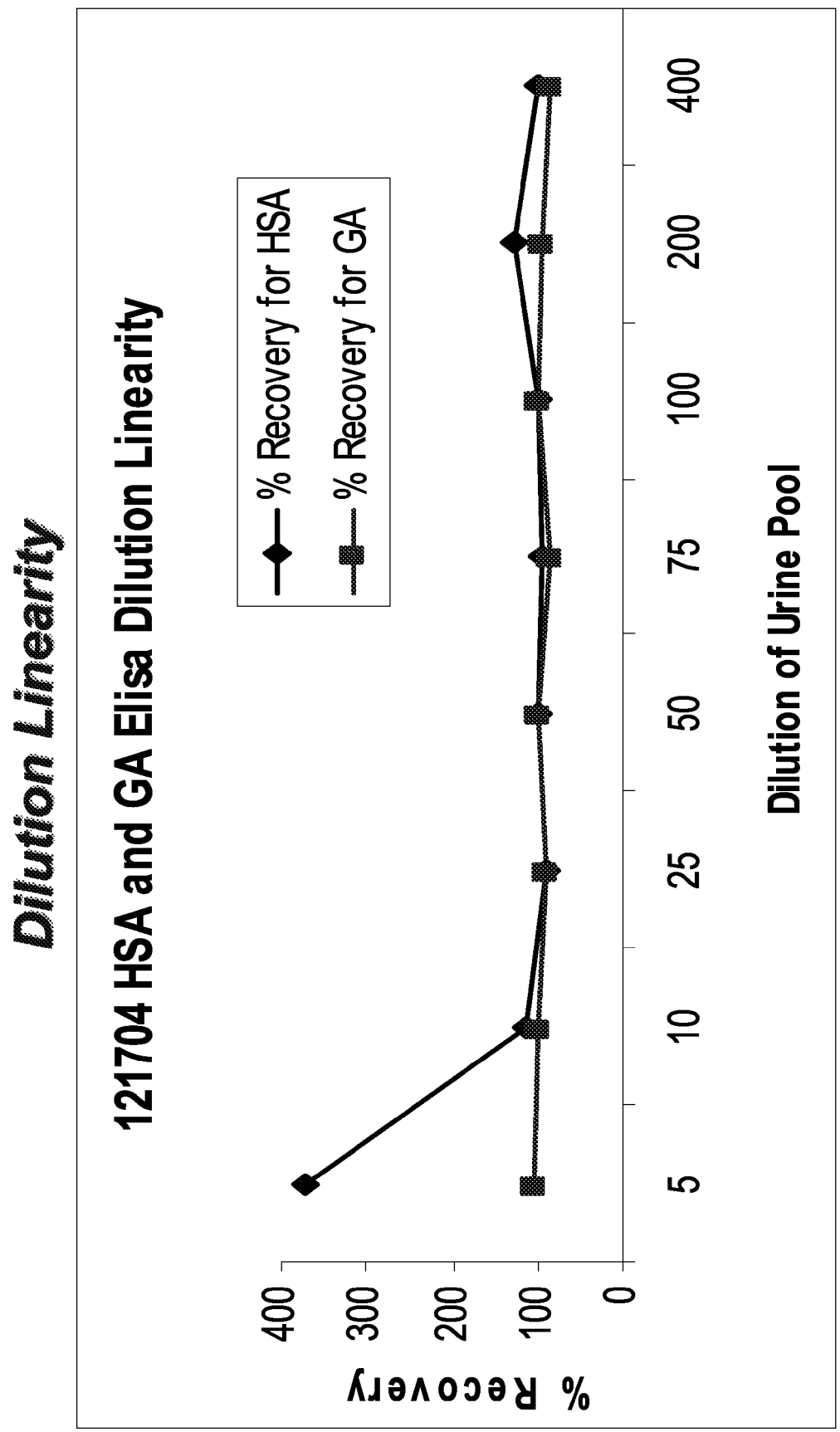
FIG. 17 shows a graph evaluating the dilution linearity of HSA and urinary protein ELISAs.

These experiments were extended to determine the dilution linearity of HSA and urinary protein ELISAs. HSA and urinary proteins were spiked into a pool of urine samples at a high concentration and then diluted with assay buffer. At each dilution of spiked analyte, the amount of HSA or urinary proteins was determined using the appropriate ELISA. The % recovery was calculated at each concentration of spiked analyte and plotted versus sample dilution. The results, shown in FIG. 17, indicated excellent dilution linearity in each ELISA In the dilution range of 1:10 to 1:400.

TABLE 1

| Sample | Analyte | 150 ug/ml Spike (% Recovery) | 50 ug/ml Spike (% Recovery) | 10 ug/ml Spike (% Recovery) | Average Spike Recovery (% Recovery) |
|---|---|---|---|---|---|
| BH | HSA | 82 | 74 | 83 | 80 |
| BH | GA | 110 | 101 | 94 | 102 |
| JL | HSA | 94 | 75 | 75 | 81 |
| JL | GA | 123 | 104 | 93 | 106 |
| SR | HSA | 94 | 104 | 107 | 102 |
| SR | GA | 102 | 106 | 102 | 103 |
| 46065 | HSA | 105 | 99 | 101 | 101 |
| 46065 | GA | 119 | 102 | 103 | 108 |
| 46086 | HSA | 94 | 97 | 99 | 97 |
| 46086 | GA | 94 | 120 | 97 | 104 |
| 46097 | HSA | 106 | 108 | 103 | 106 |
| 46097 | GA | 117 | 94 | 108 | 106 |

The interassay precision of immunoassay standards in the HSA and urinary protein ELISAs were evaluated. Interassay precision of each ELISA was determined by analysis of assay standards in 12 separate experimental runs conducted over four days. Percent coefficient of variation (% CVs) were calculated across all 12 precision runs. Within the quantifiable range of the assays (upper limit of quantitation [ULQ]—lower limit of quantitation [LLQ]), the % CVs ranged from 5.48% to 15.89% for the HSA ELISA and from 6.92% to 14.72% for the urinary protein ELISA. These results are shown in Table 2 below.

The interassay precision of sample pools in the HSA and urinary protein ELISAs were also evaluated. Interassay precision of each ELISA was determined by analysis of sample pools in six separate experimental runs conducted over three days. Percent coefficient of variation (% CVs) were calculated across all six precision runs. The % CVs ranged from 9.0% to 17.2% for the HSA ELISA and from 18.9% to 20.6% for the urinary protein ELISA. These results are shown in Table 3 below.

TABLE 2

| STANDARDS (ug/mL) | Cumulative Avg Conc. | Cumulative SD Conc. | Cumulative CV Conc. (%) | |
|---|---|---|---|---|
| INTERASSAY Precision of IBA HSA Competitive ELISA | | | | |
| 20.00 | 116.61 | 117.25 | 100.55 | |
| 6.60 | 5.83 | 0.43 | 7.36 | ULQ = 330 ug/ml |
| 2.20 | 1.89 | 0.10 | 5.48 | |
| 0.74 | 0.73 | 0.05 | 7.05 | |
| 0.25 | 0.27 | 0.02 | 7.12 | |
| 0.08 | 0.08 | 0.01 | 15.89 | |
| 0.03 | 0.02 | 0.00 | 12.74 | LLQ = .5-1.5 ug/ml |
| 0.01 | 0.01 | 0.00 | 27.57 | |
| 0.00 | 0.01 | 0.00 | 29.46 | |
| INTERASSAY Precision of IBA GA Competitive ELISA | | | | |
| 20.00 | 21.91 | 2.23 | 10.18 | ULQ = 1000 ug/ml |
| 6.60 | 6.19 | 0.59 | 9.52 | |
| 2.20 | 2.25 | 0.16 | 6.92 | |
| 0.74 | 0.74 | 0.07 | 9.10 | |
| 0.25 | 0.25 | 0.03 | 10.85 | |
| 0.08 | 0.08 | 0.01 | 14.72 | LLQ = 1.5-4 ug/ml |
| 0.03 | 0.03 | 0.01 | 26.20 | |
| 0.01 | 0.01 | 0.01 | 51.58 | |
| 0.00 | 0.02 | 0.02 | 92.48 | |

TABLE 3

| HSA ELISA | | | | | | | | |
|---|---|---|---|---|---|---|---|---|
| Dec. 14, 2004 Avg Conc. | Dec. 14, 2004 Avg Conc. | Dec. 16, 2004 Avg Conc. | Dec. 16, 2004 Avg Conc. | Dec. 17, 2004 Avg Conc. | Dec. 17, 2004 Avg Conc. | Cumulative Avg Conc. | Cumulative SD Conc. | Cumulative CV Conc (%) |
| 2.9 | 3.1 | 2.7 | 2.5 | 2.4 | 3.0 | 2.8 | 0.3 | 9.0 |
| 24.4 | 24.4 | 17.2 | 15.9 | 21.3 | 25.4 | 21.4 | 3.7 | 17.2 |
| 59.8 | 64.6 | 45.4 | 43.7 | 54.6 | 65.2 | 55.6 | 8.5 | 15.4 |

TABLE 3-continued

| | | | | | | | | |
|---|---|---|---|---|---|---|---|---|
| | | | HSA ELISA | | | | | |
| Dec. 14, 2004 Avg Conc. | Dec. 14, 2004 Avg Conc. | Dec. 16, 2004 Avg Conc. | Dec. 16, 2004 Avg Conc. | Dec. 17, 2004 Avg Conc. | Dec. 17, 2004 Avg Conc. | Cumulative Avg Conc. | Cumulative SD Conc. | Cumulative CV Conc (%) |
| 3.6 | 3.6 | 2.7 | 4.4 | 2.8 | 3.2 | 3.4 | 0.6 | 18.9 |
| 27.1 | 15.5 | 17.1 | 22.1 | 18.8 | 19.7 | 20.0 | 4.1 | 20.8 |
| 83.8 | 57.2 | 71.3 | 71.7 | 45.5 | 70.2 | 66.6 | 13.3 | 20.0 |

It should be understood that the foregoing disclosure emphasizes certain specific embodiments of the invention and that all modifications or alternatives equivalent thereto are within the spirit and scope of the invention as set forth in the appended claims.

What we claim is:

1. A mixture of polyclonal antisera for diagnosing kidney disease in a human or animal, comprising a plurality of antibodies immunologically specific for each of a plurality of proteins, wherein the plurality of proteins comprises zinc alpha-2-glycoprotein, alpha-1 microglobulin, alpha-1-acid glycoprotein 1, alpha-1-acid glycoprotein 2, IgG kappa chain (IGKV1-5), IgG lambda chain, prostaglandin-H2 D-isomerase precursor, hepatocyte growth factor-like (HGFL) protein, urine protein 1, complement regulatory protein CD59, thrombin, hemopexin, alpha-2-HS-glycoprotein precursor, G(M2)activator protein, pancreatic stone protein, saposin precursor, pepsin, kininogen, alpha-1 B-glycoprotein, beta-trace 23kD glycoprotein, haptoglobin, gelsolin, and whey acid protein, and wherein said mixture of polyclonal antisera does not immunologically cross-react with serum albumin.

2. The polyclonal antisera according to claim 1 that is adapted for use in an immunoassay.

3. The polyclonal antisera according to claim 2, wherein the immunoassay is an enzyme-linked immunoassay.

4. A diagnostic reagent comprising the mixture of polyclonal antisera of claim 1.

5. The diagnostic reagent of claim 4, wherein the polyclonal antisera are adapted for use in an immunoassay.

6. The diagnostic reagent of claim 5, wherein the immunoassay is an enzyme-linked immunoassay.

7. The diagnostic reagent of claim 6, further comprising a cognate substrate for the enzyme-linked immunoassay, wherein the enzyme-linked immunoassay produces a detectable reaction product.

8. A kit comprising the diagnostic reagent according to claim 4.

9. The kit according to claim 8, further comprising a separate reagent for determining an amount of serum albumin in a urine sample.

10. The kit according to claim 9, wherein the separate reagent for determining the amount of serum albumin is an immunological reagent.

11. The kit according to claim 8, wherein said polyclonal antisera is adapted for use in an immunoassay.

12. The kit according to claim 11, wherein the immunoassay, is an enzyme-linked immunoassay.

13. The kit according to claim 12, further comprising a cognate substrate for the enzyme-linked immunoassay, wherein the enzyme-linked immunoassay produces a detectable reaction product.

14. A diagnostic reagent comprising a mixture of polyclonal antisera or monoclonal antibodies immunologically specific for each of a plurality of proteins, wherein the plurality of proteins comprises zinc alpha-2-glycoprotein, alpha-1 microglobulin, alpha-1-acid glycoprotein 1, alpha-1-acid glycoprotein 2, IgG kappa chain (IGKV1-5), IgG lambda chain, prostaglandin-H2 D-isomerase precursor, hepatocyte growth factor-like (HGFL) protein, urine protein 1, complement regulatory protein CD59, thrombin, hemopexin, alpha-2-HS-glycoprotein precursor, G(M2)activator protein, pancreatic stone protein, saposin precursor, pepsin, kininogen, alpha-1B-glycoprotein, beta-trace 23kD glycoprotein, haptoglobin, gelsolin, and whey acid protein, and wherein the diagnostic reagent does not immunologically cross-react with serum albumin.

15. The diagnostic reagent of claim 14, wherein the mixture of polyclonal antisera or monoclonal antibodies is adapted for use in an immunoassay.

16. The diagnostic reagent of claim 15, wherein the immunoassay is an enzyme-linked immunoassay.

17. The diagnostic reagent of claim 16, further comprising a cognate substrate for the enzyme-linked immunoassay, wherein the enzyme-linked immunoassay produces a detectable reaction product.

18. A kit comprising the diagnostic reagent according to claim 14.

19. The kit according to claim 18, further comprising a separate reagent for determining an amount of serum albumin in a urine sample.

20. The kit according to claim 19, wherein the separate reagent for determining the amount of serum albumin is an immunological reagent.

21. The kit according to claim 18, wherein the mixture of polyclonal antisera or monoclonal antibodies is adapted for use in an immunoassay.

22. The kit according to claim 21, wherein the immunoassay is an enzyme-linked immunoassay.

23. The kit according to claim 22, further comprising a cognate substrate for the enzyme-linked immunoassay, wherein the enzyme-linked immunoassay produces a detectable reaction product.

* * * * *